United States Patent
Vogel et al.

(10) Patent No.: US 10,428,318 B2
(45) Date of Patent: Oct. 1, 2019

(54) MUTATED SIALIDASES

(71) Applicant: Glycom A/S, Hørsholm (DK)

(72) Inventors: Andreas Vogel, Leipzig (DE); Ramona Schmiedel, Leipzig (DE); Elise Champion, Toulouse (FR); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 95 days.

(21) Appl. No.: 15/579,843

(22) PCT Filed: Jun. 9, 2016

(86) PCT No.: PCT/IB2016/053410
§ 371 (c)(1),
(2) Date: Dec. 5, 2017

(87) PCT Pub. No.: WO2016/199069
PCT Pub. Date: Dec. 15, 2016

(65) Prior Publication Data
US 2018/0163185 A1 Jun. 14, 2018

(30) Foreign Application Priority Data
Jun. 9, 2015 (EP) .................................. 15171175

(51) Int. Cl.
| C12N 9/10 | (2006.01) |
|---|---|
| C12P 21/00 | (2006.01) |
| C07H 3/06 | (2006.01) |
| C12P 19/18 | (2006.01) |
| C12P 19/04 | (2006.01) |

(52) U.S. Cl.
CPC ................ *C12N 9/10* (2013.01); *C07H 3/06* (2013.01); *C12P 19/04* (2013.01); *C12P 19/18* (2013.01); *C12P 21/005* (2013.01)

(58) Field of Classification Search
None
See application file for complete search history.

(56) References Cited

U.S. PATENT DOCUMENTS

| 5,827,714 A | 10/1998 | Yamamoto et al. |
| 6,255,094 B1 | 7/2001 | Yamamoto et al. |
| 7,993,875 B2 | 8/2011 | Tsukamoto et al. |
| 8,187,838 B2 | 5/2012 | Tsukamoto et al. |
| 8,187,853 B2 | 5/2012 | Yamamoto et al. |
| 8,372,617 B2 | 2/2013 | Yamamoto et al. |
| 2012/0184016 A1 | 7/2012 | Mine et al. |

FOREIGN PATENT DOCUMENTS

| KR | 1020140122902 A | 10/2014 |
| KR | 1020160036391 A | 4/2016 |
| WO | 2012007588 A9 | 1/2012 |
| WO | 2012156898 A1 | 11/2012 |
| WO | 2014167112 A1 | 10/2014 |

OTHER PUBLICATIONS

Cheng, J. et al., "Trans-sialidase activity of Photobacterium damsela alpha2,6-sialyltransferase and its application in the synthesis of sialosides," Glycobiology, 2010, vol. 20(2), pp. 260-268.
Choi, Y.H. et al., "Protein engineering of alpha2,3/2,6-sialyltransferase to improve the yield and productivity of in vitro sialyllactose synthesis," Glycobiology, 2014, vol. 24(2), pp. 159-169.
Garcia-Contreras, R. et al., "Why in vivo may not equal in vitro—new effectors revealed by measurement of enzymatic activities under the same in vivo-like assay conditions," FEBS Journal, 2012, vol. 279, pp. 4145-4159.
Mine, T. et al., "An alpha2,6-sialyltransferase cloned from Photobacterium leiognathi strain JT-SHIZ-119 shows both sialyltransferase and neuraminidase activity," Glycobiology, 2010, vol. 20(2), pp. 158-165.
Schmolzer, K. et al., "Complete switch from alpha-2,3- to alpha-2,6-regioselectivity in Pasteurella dagmatis beta-D-galactoside sialyltransferase by active-site redesign," Chem. Comm., 2016, vol. 51, pp. 3083-3086.
Tsukamoto, H. et al., "*Photobacterium* sp. JT-ISH-224 Produces Two Sialyltransferases, alpha-/beta-Galactoside alpha2,3-Sialyltransferase and beta-Galactoside alpha2,6-Sialyltransferase," J. Biochem., 2008, vol. 143, pp. 187-197.
Urashima, T. et al. (2011) Nutrition and Diet Research Progress: Milk Oligosaccharides. New York: Nova Science Publishers, Inc.
Yamamoto, T. et al., "A beta-galactoside alpha2,6-sialyltransferase produced by a marine bacterium, Photobacterium leiognathi JT-SHIZ-145, is active at pH 8," Glycobiology, 2007, vol. 17(11), pp. 1167-1174.
Yamamoto, T. et al., "Cloning and Expression of a Marine Bacterial beta-Galactoside alpha2,6-Sialyltransferase Gene from Photobacterium damsela JT0160," J. Biochem., 1998, vol. 123, pp. 94-100.
Michalak, M., et al., "Biocatalytic production of 3'-sialyllactose by use of a modified sialidase with superior trans-sialidase activity," Process Biochemistry, 2014, vol. 49, pp. 265-270.
Guo, Y., et al., "Modulating the regioselectivity of a Pasteurella multocida sialyltransferase for biocatalytic production of 3'- and 6'-sialyllactose," Enzyme and Microbial Technology, 2015, vol. 78, pp. 54-62.

*Primary Examiner* — Suzanne M Noakes
*Assistant Examiner* — Jae W Lee
(74) *Attorney, Agent, or Firm* — Neal, Gerber & Eisenberg LLP

(57) ABSTRACT

The invention provides engineered enzymes of transsialidase and/or sialyl transferase activity that have increased regioselectivity and/or increased thermostability.

20 Claims, 3 Drawing Sheets
Specification includes a Sequence Listing.

```
SEQ ID NO. 1    MCNDNQNTVDVVVSTVNDNVIENNTYQVKPIDTPTTFDSYSWIQTCGTPILKDDEKYSLS  60
SEQ ID NO. 2    MCNDNQNTVDVVVSTVNDNVIENNTYQVKPIDTPTTFDSYSWIQTCGTPILKDDEKYSLS  60
SEQ ID NO. 3    MCNSDNTSLKETVSSNSADVVETETYQLTPIDAPSSFLSHSWEQTCGTPILNESDKQAIS  60

SEQ ID NO. 1    FDFVAPELDQDEKFCFEFTGDVDGKRYVTQTNLTVVAPTLEVYVDHASLPSLQQLMKIIQ  120
SEQ ID NO. 2    FDFVAPELDQDEKFCFEFTGDVDGKRYVTQTNLTVVAPTLEVYVDHASLPSLQQLMKIIQ  120
SEQ ID NO. 3    FDFVAPELKQDEKYCFTFKGITGDHRYITNTTLTVVAPTLEVYIDHASLPSLQQLIHIIQ  120

SEQ ID NO. 1    QKNEYSQNERFISWGRIGLTEDNAEKLNAHIYPLAGNNTSQELVDAVIDYADSKNRLNLE  180
SEQ ID NO. 2    QKNEYSQNERFISWGRIRLTEDNAEKLNAHIYPLAGNNTSQELVDAVIDYADSKNRLNLE  180
SEQ ID NO. 3    AKDEYPSNQRFVSWKRVTVDADNANKLNIHTYPLKGNNTSPEMVAAIDEYAQSKNRLNIE  180

SEQ ID NO. 1    LNTNTAHSFFNLAPILRIISSKSNILISNINLYDDGSAEYVNLYNWKDTEDKSVKLSDSF  240
SEQ ID NO. 2    LNTNTGHSFRNIAPILRATSSKNNILISNINLYDDGSAEYVSLYNWKDTDNKSQKLSDSF  240
SEQ ID NO. 3    FYTNTAHVFNNLPPIIQPLYNNEKVKISHISLYDDGSSEYVSLYQWKDTPNKIETLEGEV  240

SEQ ID NO. 1    LVLKDYFNGISSEKPSGIYGRYNWHQLYNTSYYFLRKDYLTVEPQLHDLREYLGGSLKQM  300
SEQ ID NO. 2    LVLKDYLNGISSEKPNGIYSIYNWHQLYHSSYYFLRKDYLTVETKLHDLREYLGGSLKQM  300
SEQ ID NO. 3    SLLANYLAGTSPDAPKGMGNRYNWHKLYDTDYYFLREDYLDVEANLHDLRDYLGSSAKQM  300

SEQ ID NO. 1    SWDGFSQLSKGDKELFLNIVGFDQEKLQQEYQQSELPNFVFTGTTTWAGGETKEYYAQQQ  360
SEQ ID NO. 2    SWDTFSQLSKGDKELFLNIVGFDQEKLQQEYQQSELPNFVFTGTTTWAGGETKEYYAQQQ  360
SEQ ID NO. 3    PWDEFAKLSDSQQTLFLDIVGFDKEQLQQQYSQSPLPNFIFTGTTTWAGGETKEYYAQQQ  360

SEQ ID NO. 1    VNVVNNAINETSPYYLGREHDLFFKGHPRGGIINDIILGSFNNMIDIPAKVSFEVLMMTG  420
SEQ ID NO. 2    VNVVNNAINETSPYYLGREHDLFFKGHPRGGIINDIILGSFNNMIDIPAKVSFEVLMMTG  420
SEQ ID NO. 3    VNVINNAINETSPYYLGKDYDLFFKGHPAGGVINDIILGSFPDMINIPAKISFEVLMMTD  420

SEQ ID NO. 1    MLPDTVGGIASSLYFSIPAEKVSFIVFTSSDTITDREDALKSPLVQVMMTLGIVKEKDVL  480
SEQ ID NO. 2    MLPDTVGGIASSLYFSIPAEKVSFIVFTSSDTITDREDALKSPLVQVMMTLGIVKEKDVL  480
SEQ ID NO. 3    MLPDTVAGIASSLYFTIPADKVNFIVFTSSDTITDREEALKSPLVQVMLTLGIVKEKDVL  480

SEQ ID NO. 1    FWSDLPDCSSGVCIAQY-------------------------------------------  497
SEQ ID NO. 2    FWC---------------------------------------------------------  483
SEQ ID NO. 3    FWADHKVNSMEVAIDEACTRIIAKRQPTASDLRLVIAIIKTITDLERIGDVAESIAKVAL  540

SEQ ID NO. 1    ------------------------------------------------------------  497
SEQ ID NO. 2    ------------------------------------------------------------  483
SEQ ID NO. 3    ESFSNKQYNLLVSLESLGQHTVRMLHEVLDAFARMDVKAAIEVYQEDDRIDQEYESIVRQ  600

SEQ ID NO. 1    ------------------------------------------------------------  497
SEQ ID NO. 2    ------------------------------------------------------------  483
SEQ ID NO. 3    LMAHMMEDPSSIPNVMKVMWAARSIERVGDRCQNICEYIIYFVKGKDVRHTKPDDFGTML  660

SEQ ID NO. 1    - 497
SEQ ID NO. 2    - 483
SEQ ID NO. 3    D 661
```

Figure 1

```
SEQ ID NO. 1     1 MCNDNQNTVDVVVSTVNDNVIENNTYQVKPIDTPTTFDSYSWIQTCGTPI   50
                   ||||||||||||||||||||||||||||||||||||||||||||||||||
SEQ ID NO. 2     1 MCNDNQNTVDVVVSTVNDNVIENNTYQVKPIDTPTTFDSYSWIQTCGTPI   50

SEQ ID NO. 1    51 LKDDEKYSLSFDFVAPELDQDEKFCFEFTGDVDGKRYVTQTNLTVVAPTL  100
                   ||||||||||||||||||||||||||||||||||||||||||||||||||
SEQ ID NO. 2    51 LKDDEKYSLSFDFVAPELDQDEKFCFEFTGDVDGKRYVTQTNLTVVAPTL  100

SEQ ID NO. 1   101 EVYVDHASLPSLQQLMKIIQQKNEYSQNERFISWGRIGLTEDNAEKLNAH  150
                   |||||||||||||||||||||||||||||||||||||.||||||||||||
SEQ ID NO. 2   101 EVYVDHASLPSLQQLMKIIQQKNEYSQNERFISWGRIRLTEDNAEKLNAH  150

SEQ ID NO. 1   151 IYPLAGNNTSQELVDAVIDYADSKNRLNLELNTNTAHSFPNLAPILRIIS  200
                   |||||||||||||||||||||||||||||||||||.|||.|:||||||..|
SEQ ID NO. 2   151 IYPLAGNNTSQELVDAVIDYADSKNRLNLELNTNTGHSFRNIAPILRATS  200

SEQ ID NO. 1   201 SKSNILISNINLYDDGSAEYVNLYNWKDTEDKSVKLSDSFLVLKDYFNGI  250
                   ||:|||||||||||||||||:|||||||::||.||||||||||||||.|||
SEQ ID NO. 2   201 SKNNILISNINLYDDGSAEYVSLYNWKDTDNKSQKLSDSFLVLKDYLNGI  250

SEQ ID NO. 1   251 SSEKPSGIYGRYNWHQLYNTSYYFLRKDYLTVEPQLHDLREYLGGSLKQM  300
                   |||||:|||..|||||||::||||||||||||.:||||||||||||||||
SEQ ID NO. 2   251 SSEKPNGIYSIYNWHQLYHSSYYFLRKDYLTVETKLHDLREYLGGSLKQM  300

SEQ ID NO. 1   301 SWDGFSQLSKGDKELFLNIVGFDQEKLQQEYQQSELPNFVFTGTTTWAGG  350
                   |||.||||||||||||||||||||||||||||||||||||||||||||||
SEQ ID NO. 2   301 SWDTFSQLSKGDKELFLNIVGFDQEKLQQEYQQSELPNFVFTGTTTWAGG  350

SEQ ID NO. 1   351 ETKEYYAQQQVNVVNNAINETSPYYLGREHDLFFKGHPRGGIINDIILGS  400
                   ||||||||||||||||||||||||||||||||||||||||||||||||||
SEQ ID NO. 2   351 ETKEYYAQQQVNVVNNAINETSPYYLGREHDLFFKGHPRGGIINDIILGS  400

SEQ ID NO. 1   401 FNNMIDIPAKVSFEVLMMTGMLPDTVGGIASSLYFSIPAEKVSFIVFTSS  450
                   ||||||||||||||||||||||||||||||||||||||||||||||||||
SEQ ID NO. 2   401 FNNMIDIPAKVSFEVLMMTGMLPDTVGGIASSLYFSIPAEKVSFIVFTSS  450

SEQ ID NO. 1   451 DTITDREDALKSPLVQVMMTLGIVKEKDVLFWSDLPDCSSGVCIAQY    497
                   |||||||||||||||||||||||||||||||.
SEQ ID NO. 2   451 DTITDREDALKSPLVQVMMTLGIVKEKDVLFWC---------------   483
```

Figure 2.

```
SEQ ID NO. 1     1 MCNDNQNTVDVVVSTVNDNVIENNTYQVKPIDTPTTFDSYSWIQTCGTPI    50
                   |||.:..:....||:.:.:|:|..||:|:|||..|:::|:|:||.|||||||
SEQ ID NO. 3     1 MCNSDNTSLKETVSSNSADVVETETYQLTPIDAPSSFLSHSWEQTCGTPI    50

SEQ ID NO. 1    51 LKDDEKYSLSFDFVAPELDQDEKFCFEFTGDVDGKRYVTQTNLTVVAPTL   100
                   |..:.:|.::|||||||||.||||:||.|.|....||:|.|.||||||||
SEQ ID NO. 3    51 LNESDKQAISFDFVAPELKQDEKYCFTFKGITGDHRYITNTTLTVVAPTL   100

SEQ ID NO. 1   101 EVYVDHASLPSLQQLMKIIQQRNEYSQNERFISWGRIGLTEDNAEKLNAH   150
                   ||||:||||||||||:.|||.|:||..|:||:||.|:.:..|||.|||.|
SEQ ID NO. 3   101 EVYIDHASLPSLQQLIHIIQAKDEYPSNQRFVSWKRVTVDADNANKLNIH   150

SEQ ID NO. 1   151 IYPLAGNNTSQELVDAVIDYADSKNRLNLELNTNTAHSFPNLAPILRIIS   200
                   .|||.|||||.|:|.|:.::||.|||||||:|..||||||.|.||.||::..:.
SEQ ID NO. 3   151 TYPLKGNNTSPEMVAAIDEYAQSKNRLNIEFYTNTAHVFNNLPPIIQPLY   200

SEQ ID NO. 1   201 SKSNILISNINLYDDGSAEYVNLYNWKDTEDKSVKLSDSFLVLKDYFNGI   250
                   :....:.||:|:||||||:||:||:||..:|...:|.:|..|.
SEQ ID NO. 3   201 NNEKVKISHISLYDDGSSEYVSLYQWKDTPNKIETLEGEVSLLANYLAGT   250

SEQ ID NO. 1   251 SSEKPSGIYGRYNWHQLYNTSYYFLRKDYLTVEPQLHDLREYLGGSLKQM   300
                   |..:.|.|:...|||||||:|.|:||:||||.:|||..|:|||.|.|.|||
SEQ ID NO. 3   251 SPDAPKGMGNRYNWHKLYDTDYYFLREDYLDVEANLHDLRDYLGSSAKQM   300

SEQ ID NO. 1   301 SWDGFSQLSKGDKELFLNIVGFDQEKLQQEYQQSELPNFVFTGTTTWAGG   350
                   .||.|::||...:.|||:|||||:|||||:|.||.||||||:|||||||||
SEQ ID NO. 3   301 PWDEFAKLSDSQQTLFLDIVGFDKEQLQQQYSQSPLPNFIFTGTTTWAGG   350

SEQ ID NO. 1   351 ETKEYYAQQQVNVVNNAINETSPYYLGPEHDLFFKGHPRGGIINDIILGS   400
                   |||||||||||||:|||||||||||:::|||||||||.||:|||||||||
SEQ ID NO. 3   351 ETKEYYAQQQVNVINNAINETSPYYLGKDYDLFFKGHPAGGVINDIILGS   400

SEQ ID NO. 1   401 FNNMIDIPAKVSFEVLMMTGMLPDTVGGIASSLYFSIPAEKVSFIVFTSS   450
                   |.:||:||||:|||||||.||||||||.||||||||:|||:||:|||||||
SEQ ID NO. 3   401 FPDMINIPAKISFEVLMMTDMLPDTVAGIASSLYFTIPADKVNFIVFTSS   450

SEQ ID NO. 1   451 DTITDREDALKSPLVQVMMTLGIVKEKDVLFWSDLPDCSSGVCIAQY----  497
                   |||||||:|||||||||||:|||||||||||||:|....|..|.|.:.
SEQ ID NO. 3   451 DTITDREEALKSPLVQVMLTLGIVKEKDVLFWADHKVNSMEVAIDEACTR   500

SEQ ID NO. 1   498 ------------------------------------------------   497
SEQ ID NO. 3   501 IIAKRQPTASDLRLVIAIIKTITDLERIGDVAESIAKVALESFSNKQYNL   550

SEQ ID NO. 1   498 ------------------------------------------------   497
SEQ ID NO. 3   551 LVSLESLGQHTVRMLHEVLDAFARMDVKAAIEVYQEDDRIDQEYESIVRQ   600

SEQ ID NO. 1   498 ------------------------------------------------   497
SEQ ID NO. 3   601 LMAHMMEDPSSIPNVMKVMWAARSIERVGDRCQNICEYIIYFVKGKDVRH   650

SEQ ID NO. 1   498 -----------        497
SEQ ID NO. 3   651 TKPDDFGTMLD        661
```

MUTATED SIALIDASES

CROSS-REFERENCE TO RELATED APPLICATIONS

This is a national stage filing in accordance with 35 U.S.C. § 371 of PCT/IB2016/053410, filed Jun. 9, 2016, which claims the benefit of the priority of European Patent Application EP 15171175.1, filed Jun. 9, 2015, the contents of each are incorporated herein by reference.

SEQUENCE LISTING

This instant application contains a Sequence Listing which has been submitted in ASCII format via EFS-Web and is hereby incorporated by reference in its entirety. Said ASCII copy, created on Dec. 1, 2017, is named 088US00_029037-8019_SequenceListing.txt, and is 14,036 bytes in size.

FIELD OF THE INVENTION

This invention relates to engineered enzymes of α2,6-transsialidase and/or α2,6-sialyl transferase activity and having increased regioselectivity and/or increased thermostability.

BACKGROUND OF THE INVENTION

Wild-type α2,6-sialyl transferases have been isolated from marine bacteria, such as *Photobacterium damselae* JT0160 (U.S. Pat. Nos. 5,827,714, 6,255,094, Yamamoto et al. *J. Biochem.* 123, 94 (1998)), and subsequently from *Photobacterium* sp. JT-ISH-224 (U.S. Pat. Nos. 7,993,875, 8,187,838, Tsukamoto et al. *J. Biochem.* 143, 187 (2008)) and subsequently from *P. leiognathi* JT-SHIZ-145 (U.S. Pat. Nos. 8,187,853, 8,372,617, Yamamoto et al. *Glycobiology* 17, 1167 (2007)) and finally from *P. leiognathi* JT-SHIZ-119 (US 2012/184016, Mine et al. *Glycobiology* 20, 158 (2010)). The α2,6-sialyl transferase from *P. leiognathi* JT-SHIZ-119 and the truncated α2,6-sialyl transferase from *Photobacterium damselae* JT0160 have been found to also have sialidase activity (US 2012/0184016, Mine et al. *Glycobiology* 20, 158 (2010), Cheng et al. *Glycobiology* 20, 260 (2010)). However, these wild-type α2,6-sialyl transferases have not been used or entirely suitable for making sialylated oligosaccharides, particularly sialylated human milk oligosaccharides (HMOs).

Mutants of such enzymes have therefore been sought, preferably having increased regioselectivity and/or increased thermostability, in particular for the enzymatic synthesis of sialylated oligosaccharides, especially sialylated HMOs.

SUMMARY OF THE INVENTION

The present invention provides an α2,6-transsialidase having an amino acid sequence that is substantially identical with the amino acid sequence of SEQ ID No. 1, and which comprises at least one of:
  at position 156, an amino acid selected from Ser, Thr, Cys, Tyr, Asn, Gln or Trp, preferably Ser, Cys or Tyr; and/or
  at position 161, an amino acid selected from Ala, Val, Ile, Leu, Phe, Tyr, Trp or Gly, preferably Phe or Gly; and/or
  at position 180, an amino acid selected from Asp, Asn, Gln, preferably Asp; and/or
  at position 186, an amino acid selected from Val, Ile, Leu, Met, Phe, Tyr, Trp, Ser, Cys or Thr, preferably Tyr, Cys or Leu; and/or
  at position 218, an amino acid selected from Val, Ile, Leu, Met, Phe, Tyr, Trp, Cys, Gly or Thr, preferably Ile, Val, Phe or Tyr; and/or
  at position 222, an amino acid selected from Gln, Asp, Glu, Cys, Thr, Phe, Tyr, Trp, Arg, Lys or His, preferably Cys, Asp, Arg or Phe; and/or
  at position 235, an amino acid selected from Arg, His, Ser, Cys, Ala, Val, Ile or Leu, preferably Arg, His, Cys or Val; and/or
  at position 242, an amino acid selected from Arg, His or Lys, preferably His; and/or
  at position 261, an amino acid selected from His, Lys, Asp, Glu, Ala, Val, Leu or Phe, preferably Asp, Phe, His or Val; and/or
  at position 315, an amino acid selected from Ser, Thr or Cys, preferably Cys; and/or
  at position 342, an amino acid selected from Ser or Cys, preferably Cys; and/or
  at position 349, an amino acid selected from Ser, Thr or Cys, preferably Ser or Cys; and/or
  at position 350, an amino acid selected from Ser, Thr, Cys, Tyr, Trp or Phe, preferably Ser, Tyr, Phe or Cys; and/or
  at position 356, an amino acid selected from Ala, Val, Ile, Leu, Phe or Trp, preferably Val or Phe; and/or
  at position 438, an amino acid selected from Arg, His or Lys, preferably His;
wherein said positions are defined by alignment of said amino acid sequence with SEQ ID No. 1 using a comparison algorithm.

Accordingly, this invention relates to a mutated, or engineered, α2,6-transsialidase having an amino acid sequence that is substantially identical with the amino acid sequence of SEQ ID No. 1, and has the following mutations (the position of mutation corresponds to alignment of the amino acid sequence with SEQ ID No. 1):
  at position 156 is substituted by Ser, Thr, Cys, Tyr, Asn, Gln or Trp, preferably Ser, Cys or Tyr; and/or
  at position 161 is substituted by Ala, Val, Ile, Leu, Phe, Tyr, Trp or Gly, preferably Phe or Gly; and/or
  at position 180 is substituted by Asp, Asn, Gln, preferably Asp; and/or
  at position 186 is substituted by Val, Ile, Leu, Met, Phe, Tyr, Trp, Ser, Cys or Thr, preferably Tyr, Cys or Leu; and/or
  at position 218 is substituted by Val, Ile, Leu, Met, Phe, Tyr, Trp, Cys, Gly or Thr, preferably Ile, Val, Phe or Tyr; and/or
  at position 222 is substituted by Gln, Asp, Glu, Cys, Thr, Phe, Tyr, Trp, Arg, Lys or His, preferably Cys, Asp, Arg or Phe; and/or
  at position 235 is substituted by Arg, His, Ser, Cys, Ala, Val, Ile or Leu, preferably Arg, His, Cys or Val; and/or
  at position 242 is substituted by Arg, His or Lys, preferably His; and/or
  at position 261 is substituted by His, Lys, Asp, Glu, Ala, Val, Leu or Phe, preferably Asp, Phe, His or Val; and/or
  at position 315 is substituted by Ser, Thr or Cys, preferably Cys; and/or
  at position 342 is substituted by Ser or Cys, preferably Cys; and/or
  at position 349 is substituted by Ser, Thr or Cys, preferably Ser or Cys; and/or
  at position 350 is substituted by Ser, Thr, Cys, Tyr, Trp or Phe, preferably Ser, Tyr, Phe or Cys; and/or at position 356 is substituted by Ala, Val, Ile, Leu, Phe or Trp, preferably Val or Phe; and/or at position 438 is substituted by Arg, His or Lys, preferably His.

The mutated proteins according to the invention show transsialidase and/or sialyl transferase activity, preferably an α2,6-transsialidase and/or α2,6-sialyl transferase activity.

Advantageously, the amino acid sequence that is to be mutated in accordance with this invention to have an α2,6-transsialidase and/or α2,6-sialyl transferase activity with improved regioselectivity is that of the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, particularly the sialyl transferase from *P. leiognathi* JT-SHIZ-119 or its Δ2-15 truncated variant.

More advantageously, the mutated α2,6-transsialidase has an amino acid sequence which is substantially identical with the amino acid sequence of SEQ ID No. 1 and which is preferably that of the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, which has been mutated at the following amino acid positions (the position of mutation corresponds to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln or Pro is substituted by Ala, Val, Ile, Leu, Phe, Tyr, Trp or Gly, preferably Phe or Gly; and/or at position 180 Glu is substituted by Asp, Asn, Gln, preferably Asp, and/or at position 186 Ala or Gly is substituted by Val, Ile, Leu, Met, Phe, Tyr, Trp, Ser, Cys or Thr, preferably Tyr, Cys or Leu; and/or at position 218 Ala or Ser is substituted by Val, Ile, Leu, Met, Phe, Tyr, Trp, Cys, Gly or Thr, preferably Ile, Val, Phe or Tyr; and/or at position 222 Asn or Ser is substituted by Gln, Asp, Glu, Cys, Thr, Phe, Tyr, Trp, Arg, Lys or His, preferably Cys, Asp, Arg or Phe; and/or at position 235 Lys or Thr is substituted by Arg, His, Ser, Cys, Ala, Val, Ile or Leu, preferably Arg, His, Cys or Val; and/or at position 242 Val or Leu is substituted by Arg, His or Lys, preferably His; and/or at position 261 Arg or Ile is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

Even more advantageously, the amino acid sequence of the mutated α2,6-transsialidase is that of the sialyl transferase from *P. leiognathi* JT-SHIZ-119 or its Δ2-15 truncated variant which is mutated at the following amino acid positions (the position of mutation corresponds to alignment of the amino acid sequence with SEQ ID No. 1):

at position 156 Gly is substituted by Ser, Cys or Tyr; and/or at position 161 Gln is substituted by Phe or Gly; and/or at position 180 Glu is substituted by Asp, and/or at position 186 Ala is substituted by Tyr, Cys or Leu; and/or at position 218 Ala is substituted by Ile, Val, Phe or Tyr; and/or at position 222 Asn is substituted by Cys, Asp, Arg or Phe; and/or at position 235 Lys is substituted by Arg, His, Cys or Val; and/or at position 242 Val is substituted by His; and/or at position 261 Arg is substituted by Asp, Phe, His or Val; and/or at position 315 Leu is substituted by Cys; and/or at position 342 Thr is substituted by Cys; and/or at position 349 Gly is substituted by Ser or Cys; and/or at position 350 Gly is substituted by Ser, Tyr, Phe or Cys; and/or at position 356 Tyr is substituted by Val or Phe; and/or at position 438 Pro is substituted by His.

Still more advantageously, the amino acid sequence of the mutated α2,6-transsialidase is that of the sialyl transferase from *P. leiognathi* JT-SHIZ-119 or its Δ2-15 truncated variant which is mutated at at least at two amino acid positions (the position of mutation corresponds to alignment of the amino acid sequence with SEQ ID No. 1) from 156, 218, 222 and 349, particularly at least at three amino acid positions from 156, 218, 222 and 349, more particularly:

at position 156 Gly is substituted by Ser, Cys or Tyr; and/or at position 218 Ala is substituted by Ile, Val, Phe or Tyr; and/or at position 222 Asn is substituted by Cys, Asp, Arg or Phe; and/or at position 349 Gly is substituted by Ser or Cys.

The invention also relates to a process for synthesizing a sialylated carbohydrate, comprising the step of reacting a sialyl donor and a carbohydrate acceptor in the presence of the mutated (engineered) α2,6-transsialidase of the invention to transfer the sialyl residue of the sialyl donor to the carbohydrate acceptor.

The invention further relates to use of the mutated (engineered) α2,6-transsialidase of the invention for the preparation of a sialylated carbohydrate, preferably a sialylated human milk oligosaccharide having a 6-sialyl residue.

BRIEF DESCRIPTION OF THE FIGURES

The following figures are intended to illustrate the invention further. They are not intended to limit the subject matter of the invention.

FIG. 1: shows the sequences and alignment of 3 α2,6-sialyl transferases: *P. leiognathi* JT-SHIZ-119 sialyl transferase truncated by its signal peptide (Δ2-15) (SEQ ID No. 1), *P. leiognathi* JT-SHIZ-145 sialyl transferase truncated by its signal peptide (Δ2-15) (SEQ ID No. 2) and *P. damselae* JT0160 sialyl transferase truncated by its signal peptide (Δ2-15) (SEQ ID No. 3). Sequences were aligned by Multiple Sequence Alignment (MSA) using CLUSTAL Omega (1.2.1).

FIG. 2: shows the sequences and alignment of 2 α2,6-sialyl transferases: *P. leiognathi* JT-SHIZ-119 sialyl transferase truncated by its signal peptide (Δ2-15) (being SEQ ID No. 1) and *P. leiognathi* JT-SHIZ-145 sialyl transferase truncated by its signal peptide (Δ2-15) (SEQ ID No. 2). The sequences were aligned by Pairwise Sequence Alignment using EMBOSS Needle.

FIG. 3: shows the sequences and alignment of 2 α2,6-sialyl transferases: *P. leiognathi* JT-SHIZ-119 sialyl transferase truncated by its signal peptide (Δ2-15) (being SEQ ID No. 1) and *P. damselae* JT0160 sialyl transferase truncated by its signal peptide (Δ2-15) (SEQ ID No. 3). The sequences were aligned by Pairwise Sequence Alignment using EMBOSS Needle.

DETAILED DESCRIPTION OF THE INVENTION

It has now been found that all four *Photobacterium* sialyl transferases mentioned above, but truncated by their signal peptides, namely the Δ2-15 truncated sialyl transferase from *P. leiognathi* JT-SHIZ-119, the Δ2-15 truncated sialyl transferase from *P. leiognathi* JT-SHIZ-145, the Δ2-15 truncated sialyl transferase from *P. damselae* JT0160 and the Δ2-17 truncated sialyl transferase from *Photobacterium* sp. JT-ISH-224, show a transsialidase activity in addition to their sialyl transferase activity, that is they are able to transfer the sialyl residue of a sialylated oligosaccharide to an acceptor by transsialylation. This has been demonstrated in a reaction in which 6'-SL served as sialyl donor and LNnT served as sialyl acceptor to make sialylated LNnT. Although the reaction is stereoselective, that is only α2,6-sialylated products are detectable, the regioselectivity is poor, since any of the two galactosyl residues of LNnT, or both, are sialylated (Scheme 1). Compound A is LST c, a sialylated oligosaccharide occurring in human milk, whereas compounds B and C are not natural human milk oligosaccharides.

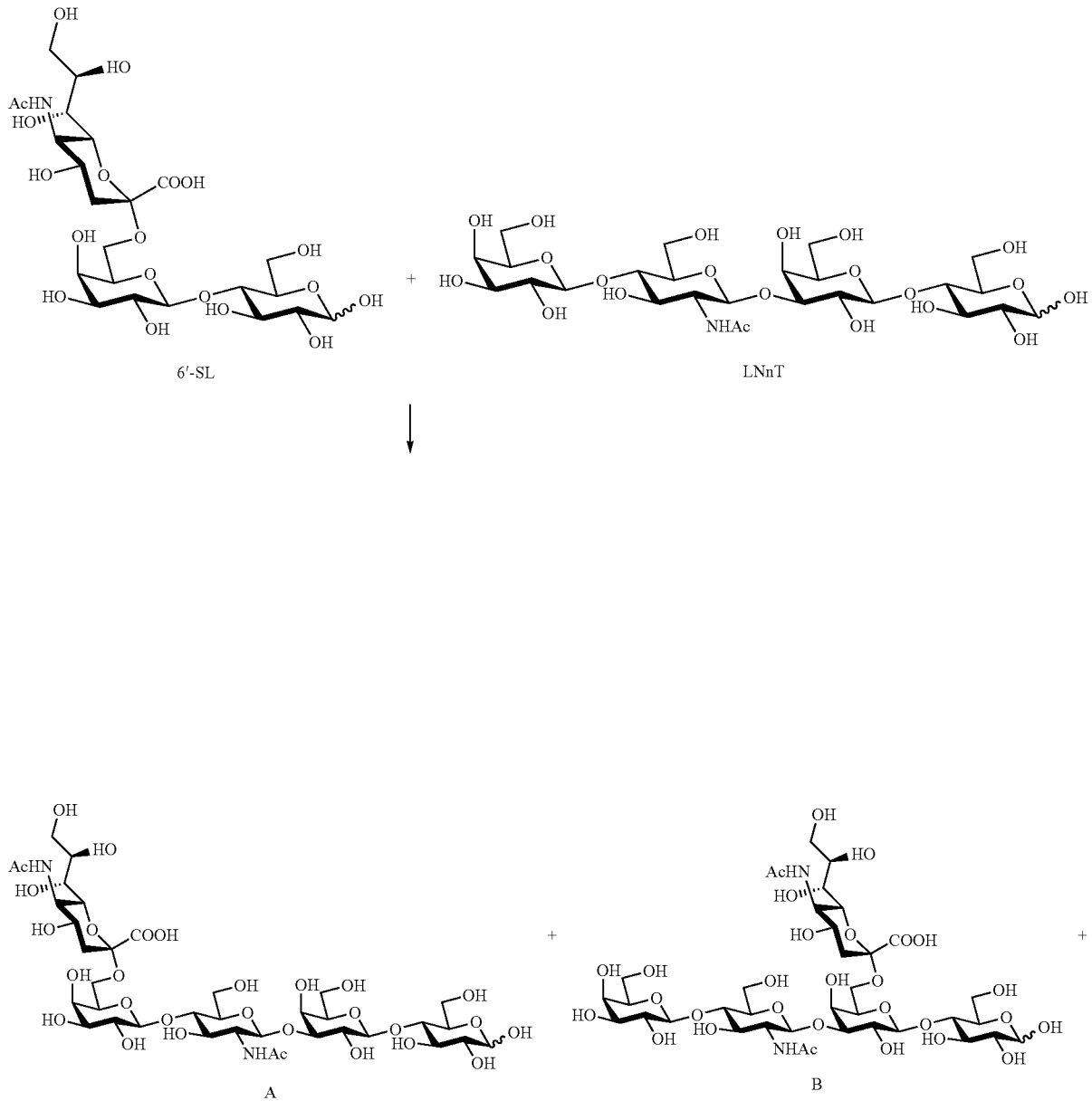

Scheme 1.

-continued

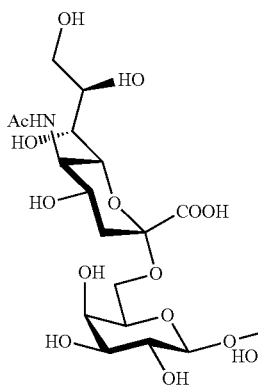
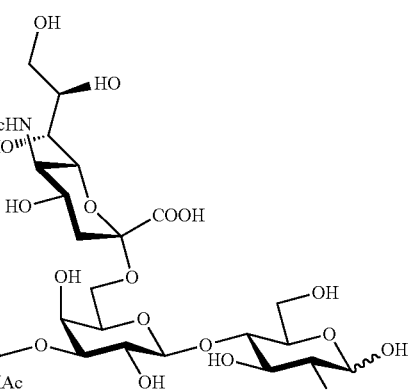

C

The Δ2-15 truncated sialyl transferase from *P. leiognathi* JT-SHIZ-145 produced a molar product ratio of compound A:compound B:compound C≈46:53:1 with ~17% of overall conversion after 4 hours. Likewise, the Δ2-15 truncated sialyl transferase from *P. damselae* JT0160 produced all three sialylated products with a slight preference for compound A, and the Δ2-17 truncated sialyl transferase from *Photobacterium* sp. JT-ISH-224 and the Δ2-15 truncated sialyl transferase from *P. leiognathi* JT-SHIZ-119 also produced all three sialylated products with a stronger preference for compound A compared to the *P. damselae* JT0160 enzyme. In all these reactions no significant hydrolysis was detectable.

Surprisingly, it has now also been discovered that certain artificially mutated α2,6-transsialidases show, in transsialidation reactions, an improved regioselectivity towards the terminal galactosyl moiety vs an internal galactosyl moiety of the acceptor compared to the wild-type (non-mutated) parent enzyme having α2,6-transsialidase and/or α2,6-sialyl transferase activity from which the mutants stem. Specifically, such α2,6-transsialidase mutants show better regioselectivity towards compound A and consequently provide a significantly higher ratio of compound A relative to compound B and/or compound C.

Accordingly, a first aspect of the invention relates to a mutated α2,6-transsialidase having an amino acid sequence which is substantially identical with SEQ ID No. 1 (i.e. has at least 60 percent (%) identity with the amino acid sequence of SEQ ID No. 1), and has been mutated (i.e. one amino acid has been replaced by another amino acid) at one or more amino acid positions (numbering corresponding to alignment of the amino acid sequence with SEQ ID No. 1) as follows:

156 which is substituted by Ser, Thr, Cys, Tyr, Asn, Gln or Trp, preferably Ser, Cys or Tyr;
161 which is substituted by Ala, Val, Ile, Leu, Phe, Tyr, Trp or Gly, preferably Phe or Gly;
180 which is substituted by Asp, Asn, Gln, preferably Asp;
186 which is substituted by Val, Ile, Leu, Met, Phe, Tyr, Trp, Ser, Cys or Thr, preferably Tyr, Cys or Leu;
218 which is substituted by Val, Ile, Leu, Met, Phe, Tyr, Trp, Cys, Gly or Thr, preferably Ile, Val, Phe or Tyr;
222 which is substituted by Gln, Asp, Glu, Cys, Thr, Phe, Tyr, Trp, Arg, Lys or His, preferably Cys, Asp, Arg or Phe;
235 which is substituted by Arg, His, Ser, Cys, Ala, Val, Ile or Leu, preferably Arg, His, Cys or Val;
242 which is substituted by Arg, His or Lys, preferably His;
261 which is substituted by His, Lys, Asp, Glu, Ala, Val, Leu or Phe, preferably Asp, Phe, His or Val;
315 which is substituted by Ser, Thr or Cys, preferably Cys;
342 which is substituted by Ser or Cys, preferably Cys;
349 which is substituted by Ser, Thr or Cys, preferably Ser or Cys;
350 which is substituted by Ser, Thr, Cys, Tyr, Trp or Phe, preferably Ser, Tyr, Phe or Cys;
356 which is substituted by Ala, Val, Ile, Leu, Phe or Trp, preferably Val or Phe; or
438 which is substituted by Arg, His or Lys, preferably His.

The amino acid sequence of SEQ ID No. 1 corresponds to the amino acid sequence of the *P. leiognathi* JT-SHIZ-119 sialyl transferase truncated by its signal peptide (Δ2-15).

The mutated α2,6-transsialidases defined above show improved regioselectivity in comparison with the wild-type (non-mutated) parent enzyme having an identical amino acid sequence with that of SEQ ID No. 1 or other corresponding wild-type (non-mutated) enzymes having an amino acid sequence which is substantially identical with SEQ ID No. 1, and from which wild-type enzymes the mutants stem.

Furthermore, the mutated α2,6-transsialidases according to the invention show not only a transsialidase, preferably an α2,6-transsialidase, activity, but also a sialyl transferase, preferably an α2,6-sialyl transferase, activity.

In accordance with this invention, the terms "substantial identity" and "substantially identical" in the context of two or more nucleic acid or amino acid sequences preferably mean that the two or more sequences are the same or have at least about 60% of nucleotides or amino acid residues in common when compared and aligned for maximum correspondence over a comparison window or designated sequences of nucleic acids or amino acids (i.e. the sequences have at least about 60 percent (%) identity). Percent identity of nucleic acid or amino acid sequences can be measured using a BLAST 2.0 sequence comparison algorithms with default parameters, or by manual alignment and visual inspection. In accordance with this invention, the percent identity of either: i) a polypeptide fragment that is "substantially identical" with a polypeptide of SEQ ID No. 1 or ii) a nucleic acid sequence that encodes a polypeptide fragment and that is "substantially identical" with a nucleic acid sequence encoding a polypeptide of SEQ ID No. 1 is preferably at least 65%, more preferably at least 70%, still more preferably at least 75%, even more preferably at least 80%, yet more preferably at least 85%, still even more preferably at least 90%, yet even more preferably at least 92%, especially at least 93%, more especially at least 94%, even more especially at least 95%, yet even more especially at least 96%, particularly at least 97%, more particularly at least 98%, and most particularly at least 99% identical to SEQ ID No 1. This definition also applies to the complement of a test sequence and to sequences that have deletions and/or additions, as well as those that have substitutions. In this regard, the position of a mutation in the amino acid sequence of the engineered (mutated) transsialidases of the invention with reference to SEQ ID No. 1 means that the position is defined by alignment of the test transsialidase sequence with SEQ ID No. 1 using either a protein sequence comparison algorithm or by manual alignment and visual inspection mentioned above. Examples of such aligned sequences are shown in FIG. 1-3. An example of an algorithm that is suitable for determining percent identity, sequence similarity and for alignment is the BLAST 2.2.20+ algorithm, which is described in Altschul et al. *Nucl. Acids Res.* 25, 3389 (1997). BLAST 2.2.20+ is used to determine percent sequence identity for the nucleic acids and proteins of the invention. Software for performing BLAST analyses is publicly available through the National Center for Biotechnology Information. Examples of sequence alignment algorithms are CLUSTAL Omega, EMBOSS Needle, MAFFT or MUSCLE.

The preferred wild type α2,6-sialyl transferases with a substantially identical amino acid sequence with SEQ ID No. 1, that is having at least about 60 percent sequence identity (determined by BLAST) with SEQ ID No. 1, are listed in Table 1.

truncated variant, having the following mutations (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln or Pro is substituted by Ala, Val, Ile, Leu, Phe, Tyr, Trp or Gly, preferably Phe or Gly; and/or at position 180 Glu is substituted by Asp, Asn, Gln, preferably Asp, and/or at position 186 Ala or Gly is substituted by Val, Ile, Leu, Met, Phe, Tyr, Trp, Ser, Cys or Thr, preferably Tyr, Cys or Leu; and/or at position 218 Ala or Ser is substituted by Val, Ile, Leu, Met, Phe, Tyr, Trp, Cys, Gly or Thr, preferably Ile, Val, Phe or Tyr; and/or at position 222 Asn or Ser is substituted by Gln, Asp, Glu, Cys, Thr, Phe, Tyr, Trp, Arg, Lys or His, preferably Cys, Asp, Arg or Phe; and/or at position 235 Lys or Thr is substituted by Arg, His, Ser, Cys, Ala, Val, Ile or Leu, preferably Arg, His, Cys or Val; and/or at position 242 Val or Leu is substituted by Arg, His or Lys, preferably His; and/or at position 261 Arg or Ile is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or

TABLE 1

| Description | Identity | Accession Number |
| --- | --- | --- |
| α2,6-sialyl transferase [*Photobacterium leiognathi*] | 100% | BAI49484.1 |
| α2,6-sialyl transferase [*Photobacterium leiognathi*] | 96% | BAF91416.1 |
| Chain A, crystal structure of sialyl transferase from *Photobacterium damselae*, residues 113-497 | 70% | 4R9V_A |
| sialyl transferase 0160 [*Photobacterium damselae*] | 68% | WP_005298232.1 |
| Chain A, crystal structure of sialyl transferase from *Photobacterium damselae* | 67% | 4R83_A |
| sialyl transferase 0160 [*Photobacterium damselae*] | 66% | BAA25316.1 |

Preferably, α2,6-sialyl transferases with a substantially identical amino acid sequence with SEQ ID No. 1 that are to be mutated in accordance with this invention to have an α2,6-transsialidase and/or α2,6-sialyl transferase activity with improved regioselectivity, are the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, more preferably the sialyl transferase from *P. leiognathi* JT-SHIZ-119 or its Δ2-15 truncated variant.

In the mutated α2,6-transsialidase of this invention, the amino acid sequence which is substantially identical with the amino acid sequence of SEQ ID No. 1 is preferably the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 at position 438 Pro is substituted by Arg, His or Lys, preferably His.

Preferably, in the mutated α2,6-transsialidase of this invention, the amino acid sequence which is substantially identical with the amino acid sequence of SEQ ID No. 1 is an amino acid sequence which is at least 90% identical with the amino acid sequence of SEQ ID No. 1, more preferably the amino acid sequence of the sialyl transferase from *P. leiognathi* JT-SHIZ-119 or its Δ2-15 truncated variant, or the sialyl transferase from *P. leiognathi* JT-SHIZ-145 or its Δ2-15 truncated variant, particularly the sialyl transferase from *P. leiognathi* JT-SHIZ-119 or its Δ2-15 truncated variant, and has mutation(s) at the following amino acid positions (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or
at position 161 Gln is substituted by Ala, Val, Ile, Leu, Phe, Tyr, Trp or Gly, preferably Phe or Gly; and/or at position 180 Glu is substituted by Asp, Asn, Gln, preferably Asp, and/or at position 186 Ala or Gly is substituted by Val, Ile, Leu, Met, Phe, Tyr, Trp, Ser, Cys, or Thr, preferably Tyr, Cys or Leu; and/or at position 218 Ala is substituted by Val, Ile, Leu, Met, Phe, Tyr, Trp, Cys, Gly or Thr, preferably Ile, Val, Phe or Tyr; and/or at position 222 Asn or Ser is substituted by Gln, Asp, Glu, Cys, Thr, Phe, Tyr, Trp, Arg, Lys or His, preferably Cys, Asp, Arg or Phe; and/or at position 235 Lys is substituted by Arg, His, Ser, Cys, Ala, Val, Ile or Leu, preferably Arg, His, Cys or Val; and/or at position 242 Val is substituted by Arg, His or Lys, preferably His; and/or at position 261 Arg or Ile is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

More preferably, in the mutated α2,6-transsialidase of this invention, the amino acid sequence which is at least 90% identical with the amino acid sequence of SEQ ID No. 1 is the sialyl transferase from *P. leiognathi* JT-SHIZ-119 or its Δ2-15 truncated variant, and is mutated at the following amino acid positions (numbering corresponding to alignment of the amino acid sequence with SEQ ID No. 1):

at position 156 Gly is substituted by Ser, Thr, Cys, Tyr, Asn, Gln or Trp, preferably Ser, Cys or Tyr; and/or at position 161 Gln is substituted by Ala, Val, Ile, Leu, Phe, Tyr, Trp or Gly, preferably Phe or Gly; and/or at position 180 Glu is substituted by Asp, Asn, Gln, preferably Asp, and/or at position 186 Ala is substituted by Val, Ile, Leu, Met, Phe, Tyr, Trp, Ser, Cys or Thr, preferably Tyr, Cys or Leu; and/or at position 218 Ala is substituted by Val, Ile, Leu, Met, Phe, Tyr, Trp, Cys, Gly or Thr, preferably Ile, Val, Phe or Tyr; and/or at position 222 Asn is substituted by Gln, Asp, Glu, Cys, Thr, Phe, Tyr, Trp, Arg, Lys or His, preferably Cys, Asp, Arg or Phe; and/or at position 235 Lys is substituted by Arg, His, Ser, Thr, Cys, Ala, Val, Ile or Leu, preferably Arg, His, Cys or Val; and/or at position 242 Val is substituted by Arg, His or Lys, preferably His; and/or at position 261 Arg is substituted by His, Lys, Asp, Glu, Ala, Val, Leu or Phe, preferably Asp, Phe, His or Val; and/or at position 315 Leu is substituted by Ser, Thr or Cys, preferably Cys; and/or at position 342 Thr is substituted by Ser or Cys, preferably Cys; and/or at position 349 Gly is substituted by Ser, Thr or Cys, preferably Ser or Cys; and/or at position 350 Gly is substituted by Ser, Thr, Cys, Tyr, Trp or Phe, preferably Ser, Tyr, Phe or Cys; and/or at position 356 Tyr is substituted by Ala, Val, Ile, Leu, Phe or Trp, preferably Val or Phe; and/or at position 438 Pro is substituted by Arg, His or Lys, preferably His.

Also preferably, in the mutated α2,6-transsialidase of this invention, the amino acid sequence which is substantially identical, particularly at least 90% identical, with SEQ ID No. 1 has at least two, preferably at least three, mutations at amino acid positions selected from the group consisting of amino acid positions as follows (numbering corresponding to alignment of the amino acid sequence with SEQ ID No. 1):

156 which is substituted by Ser, Thr, Cys, Tyr, Asn, Gln or Trp, preferably Ser, Cys or Tyr;

161 which is substituted by Ala, Val, Ile, Leu, Phe, Tyr, Trp or Gly, preferably Phe or Gly;

180 which is substituted by Asp, Asn, Gln, preferably Asp;

186 which is substituted by Val, Ile, Leu, Met, Phe, Tyr, Trp, Ser, Cys or Thr, preferably Tyr, Cys or Leu;

218 which is substituted by Val, Ile, Leu, Met, Phe, Tyr, Trp, Cys, Gly or Thr, preferably Ile, Val, Phe or Tyr;

222 which is substituted by Gln, Asp, Glu, Cys, Thr, Phe, Tyr, Trp, Arg, Lys or His, preferably Cys, Asp, Arg or Phe;

235 which is substituted by Arg, His, Ser, Cys, Ala, Val, Ile or Leu, preferably Arg, His, Cys or Val;

242 which is substituted by Arg, His or Lys, preferably His;

261 which is substituted by His, Lys, Asp, Glu, Ala, Val, Leu or Phe, preferably Asp, Phe, His or Val;

315 which is substituted by Ser, Thr or Cys, preferably Cys;

342 which is substituted by Ser or Cys, preferably Cys;

349 which is substituted by Ser, Thr or Cys, preferably Ser or Cys;

350 which is substituted by Ser, Thr, Cys, Tyr, Trp or Phe, preferably Ser, Tyr, Phe or Cys;

356 which is substituted by Ala, Val, Ile, Leu, Phe or Trp, preferably Val or Phe; and 438 which is substituted by Arg, His or Lys, preferably His.

These mutated α2,6-transsialidases are characterized by even more improved regioselectivity towards the terminal galactosyl moiety vs an internal galactosyl moiety of the acceptor compared to the one-point mutated enzymes disclosed above in transsialidase and/or sialyl transferase reactions.

According to a preferred embodiment, in the mutated α2,6-transsialidase of this invention, the amino acid sequence which is substantially identical, particularly at least 90% identical, with SEQ ID No. 1 has at least two, preferably at least three, mutations at amino acid positions selected from the group consisting of amino acid positions as follows (numbering corresponding to alignment of the amino acid sequence with SEQ ID No. 1):

substitution of the amino acid at position 156 by Ser, Thr, Cys, Tyr, Asn, Gln or Trp, preferably Ser, Cys or Tyr;

substitution of the amino acid at position 218 by Val, Ile, Leu, Met, Phe, Tyr, Trp, Cys, Gly or Thr, preferably Ile, Val, Phe or Tyr;

substitution of the amino acid at position 222 by Gln, Asp, Glu, Cys, Thr, Phe, Tyr, Trp, Arg, Lys or His, preferably Cys, Asp, Arg or Phe; and substitution of the amino acid at position 349 is substituted by Ser, Thr or Cys, preferably Ser or Cys.

According to a more preferred embodiment, in the mutated α2,6-transsialidase of this invention, the amino acid sequence which is substantially identical with the amino acid sequence of SEQ ID No. 1, is preferably the amino acid sequence of the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, and has at least two, preferably at least three, mutations at amino acid positions selected from the group consisting of the following positions as follows (numbering corresponding to alignment of the amino acid sequence with SEQ ID No. 1):
- at position 156 Gly is substituted by Ser, Thr, Cys, Tyr, Asn, Gln or Trp, preferably Ser, Cys or Tyr
- at position 218 Ala or Ser is substituted by Val, Ile, Leu, Met, Phe, Tyr, Trp, Cys, Gly or Thr, preferably Ile, Val, Phe or Tyr;
- at position 222 Asn or Ser is substituted by Gln, Asp, Glu, Cys, Thr, Phe, Tyr, Trp, Arg, Lys or His, preferably Cys, Asp, Arg or Phe; and
- at position 349 Gly is substituted by Ser, Thr or Cys, preferably Ser or Cys.

According to a yet more preferred embodiment, in the mutated α2,6-transsialidase of this invention, the amino acid sequence which is substantially identical, particularly at least 90% identical, with the amino acid sequence of SEQ ID No. 1 is preferably the sialyl transferase from *P. leiognathi* JT-SHIZ-119 or its Δ2-15 truncated variant, or the sialyl transferase from *P. leiognathi* JT-SHIZ-145 or its Δ2-15 truncated variant, and has at least two, preferably at least three, mutations at amino acid positions selected from the group consisting of the following positions (numbering corresponding to alignment of the amino acid sequence with SEQ ID No. 1):
- at position 156 Gly is substituted by Ser, Thr, Cys, Tyr, Asn, Gln or Trp, preferably Ser, Cys or Tyr
- at position 218 Ala is substituted by Val, Ile, Leu, Met, Phe, Tyr, Trp, Cys, Gly or Thr, preferably Ile, Val, Phe or Tyr;
- at position 222 Asn or Ser is substituted by Gln, Asp, Glu, Cys, Thr, Phe, Tyr, Trp, Arg, Lys or His, preferably Cys, Asp, Arg or Phe; and
- at position 349 Gly is substituted by Ser, Thr or Cys, preferably Ser or Cys.

According to an even more preferred embodiment, in the mutated α2,6-transsialidase of this invention, the amino acid sequence which is substantially identical, particularly at least 90% identical, with the amino acid sequence of SEQ ID No. 1 is preferably the sialyl transferase from *P. leiognathi* JT-SHIZ-119 or its Δ2-15 truncated variant, but has at least two, preferably at least three, mutations at amino acid positions selected from the group consisting of the following positions as follows (numbering corresponding to alignment of the amino acid sequence with SEQ ID No. 1):
- at position 156 Gly is substituted by Ser, Thr, Cys, Tyr, Asn, Gln or Trp, preferably Ser, Cys or Tyr
- at position 218 Ala is substituted by Val, Ile, Leu, Met, Phe, Tyr, Trp, Cys, Gly or Thr, preferably Ile, Phe or Tyr;
- at position 222 Asn is substituted by Gln, Asp, Glu, Cys, Thr, Phe, Tyr, Trp, Arg, Lys or His, preferably Cys, Asp, Arg or Phe; and
- at position 349 Gly is substituted by Ser, Thr or Cys, preferably Ser or Cys.

According to an especially preferred embodiment, in the mutated α2,6-transsialidase of this invention, the amino acid sequence which is substantially identical, particularly at least 90% identical, with the amino acid sequence of SEQ ID No. 1 is the sialyl transferase from *P. leiognathi* JT-SHIZ-119 or its Δ2-15 truncated variant, and contains the following mutations: A218Y, N222R and G349S (numbering corresponding to alignment of the amino acid sequence with SEQ ID No. 1).

Also in accordance with the first aspect of this invention the mutated α2,6-transsialidase of this invention has:
a) an amino acid sequence which is substantially identical with the amino acid sequence of SEQ ID No. 1, preferably the amino acid sequence of the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant,
b) at least one mutation at an amino acid position selected from the group consisting of amino acid positions as follows (numbering corresponding to alignment of the amino acid sequence with SEQ ID No. 1):
  position 156 where Gly is substituted by Ser, Thr, Cys, Tyr, Asn, Gln or Trp, preferably Ser, Cys or Tyr;
  position 161 where Gln or Pro is substituted by Ala, Val, Ile, Leu, Phe, Tyr, Trp or Gly, preferably Phe or Gly;
  position 180 where Glu is substituted by Asp, Asn, Gln, preferably Asp;
  position 186 where Ala or Gly is substituted by Val, Ile, Leu, Met, Phe, Tyr, Trp, Ser, Cys or Thr, preferably Tyr, Cys or Leu;
  position 218 where Ala or Ser is substituted by Val, Ile, Leu, Met, Phe, Tyr, Trp, Cys, Gly or Thr, preferably Ile, Val, Phe or Tyr;
  position 222 where Asn or Ser is substituted by Gln, Asp, Glu, Cys, Thr, Phe, Tyr, Trp, Arg, Lys or His, preferably Cys, Asp, Arg or Phe;
  position 235 where Lys or Thr is substituted by Arg, His, Ser, Cys, Ala, Val, Ile or Leu, preferably Arg, His, Cys or Val;
  position 242 where Val or Leu is substituted by Arg, His or Lys, preferably His;
  position 261 where Arg or Ile is substituted by His, Lys, Asp, Glu, Ala, Val, Leu or Phe, preferably Asp, Phe, His or Val;
  position 315 where Leu is substituted by Ser, Thr or Cys, preferably Cys;
  position 342 where Thr is substituted by Ser or Cys, preferably Cys;
  position 349 where Gly is substituted by Ser, Thr or Cys, preferably Ser or Cys;
  position 350 where Gly is substituted by Ser, Thr, Cys, Tyr, Trp or Phe, preferably Ser, Tyr, Phe or Cys;
  position 356 where Tyr is substituted by Ala, Val, Ile, Leu, Phe or Trp, preferably Val or Phe; and
  position 438 where Pro is substituted by Arg, His or Lys, preferably His;
c) and a further mutation at position 353, 400, 412 or 450 to 458.

Surprisingly, it has been also found that all the mutated α2,6-transsialidases (as discussed above), while providing improved regioselectivity as mentioned above, show enhanced stability, preferably enhanced thermostability, which allows the synthesis of a sialylated product to be carried out effectively under more stringent conditions, particularly higher temperatures, which frequently leads to faster reaction times. Preferred positions for mutation(s) with regard to increased thermostability may be selected from amino acid positions 353, 400, 412, 451, 452 and 458 (the position of mutation corresponds to that aligned with SEQ ID No. 1), and particularly preferred mutation(s) may be selected from the following group: K353I, S400Y, S412P, D451K, D451L, D451M, T452V, D458R and/or D458F.

Accordingly, a preferred mutated α2,6-transsialidase of this invention has:
a) an amino acid sequence that is substantially identical, particularly at least 90% identical, with the amino acid sequence of SEQ ID No. 1, preferably the amino acid sequence of the sialyl transferase from *P. leiognathi* JT-SHIZ-119 or its Δ2-15 truncated variant, or the sialyl transferase from *P. leiognathi* JT-SHIZ-145 or its Δ2-15 truncated variant, more preferably of the sialyl transferase from *P. leiognathi* JT-SHIZ-119 or its Δ2-15 truncated variant,
b) at least two, preferably three mutations, at amino acid positions selected from the group consisting of amino acid positions as follows (numbering corresponding to alignment of the amino acid sequence with SEQ ID No. 1):
position 156 where Gly is substituted by Ser, Thr, Cys, Tyr, Asn, Gln or Trp, preferably Ser, Cys or Tyr;
position 218 where Ala is substituted by Val, Ile, Leu, Met, Phe, Tyr, Trp, Cys, Gly or Thr, preferably Ile, Val, Phe or Tyr;
position 222 where Asn or Ser is substituted by Gln, Asp, Glu, Cys, Thr, Phe, Tyr, Trp, Arg, Lys or His, preferably Cys, Asp, Arg or Phe; and
position 349 where Gly is substituted by Ser, Thr or Cys, preferably Ser or Cys; preferably the following mutations: A218Y, N222R and G349S, and
c) a further mutation at position 353, 400, 412 or 450 to 458.

A more preferred mutant α2,6-transsialidase of this invention
a) is the sialyl transferase from *Photobacterium* leiognathi JT-SHIZ-119 or its Δ2-15 truncated variant, which
b) has the following mutations: A218Y, N222R and G349S, and
c) has at least one of the following mutations: K353I, S400Y, S412P, D451K, D451L, D451M, T452V, D458R and D458F.

An even more preferred mutated α2,6-transsialidase of this invention is the sialyl transferase from *Photobacterium* leiognathi JT-SHIZ-119 or its Δ2-15 truncated variant which has been mutated as follows: A218Y, N222R, G349S, S412P and D451K.

According to a second aspect of the invention, a method is provided for making a mutated α2,6-transsialidase of the first aspect of the invention, comprising the steps of
a) providing a DNA sequence encoding said mutated α2,6-transsialidase, then
b) expressing said mutated α2,6-transsialidase in a host cell transformed with the DNA sequence obtained in step a).

Step a) can be carried out in a conventional manner by making a DNA sequence that encodes a mutated α2,6-transsialidase of the invention. In step b) the so-created DNA sequence is then introduced at the gene level by usual molecular-biological methods. The DNA sequence of the enzyme variants can be cloned in an expression vector which can be introduced in an appropriate host expression strain such as *E. coli*, containing DNA plasmids with the required information for regulation of expression of the enzyme variant. The sequence encoding the enzyme variant can be placed under the control of an inducible promoter. As a result, by adding an inducer, the expression of the enzyme variant can be controlled (generally, isopropyl-β-D-thiogalactopyranoside (IPTG) is used). The so-transformed host cells are then cultured in conventional nutrient media (e.g. Lennox broth, minimal medium M9) and induced with IPTG. After expression, the biomass can be harvested by centrifugation. The mutated enzyme can be isolated from the biomass after appropriate cell lysis and purification. In this process, conventional centrifugation, precipitation, ultrafiltration and/or chromatographic methods can be used.

According to a third aspect of the invention, a method is provided for synthesizing a sialylated saccharide or glycoconjugate by reacting a sialyl donor and a saccharide or glycoconjugate acceptor in the presence of a mutated α2,6-transsialidase of the first aspect of the invention, whereby the sialyl residue of the sialyl donor is transferred to the saccharide or glycoconjugate acceptor.

The saccharide acceptor used in the third aspect of the invention can be any mono- or oligosaccharide, or the glycoconjugate acceptor (such as glycoproteins, glycopeptides, peptidoglycans, glycolipids, lipopolysaccharides, etc.) can comprise any mono- or oligosaccharide. The oligosaccharide acceptor or the oligosaccharide fragment of the glycoconjugate acceptor preferably comprises 2-10, more preferably 2-6, particularly 2-4 monosaccharide units, and preferably contains a galactose unit, more preferably a terminal galactose unit at the non-reducing end. Even more preferably said galactose unit either forms a N-acetyl-lactosaminyl (Galpβ1-4GlcNAcp) or a lacto-N-biosyl (Galpβ1-3GlcNAcp) fragment with an adjacent N-acetyl-glucosamine or a lactosyl fragment with a glucose unit which glucose is advantageously at the reducing end. Particularly, the oligosaccharide acceptor is lactose, or comprises a N-acetyl-lactosaminyl or lacto-N-biosyl moiety and is of formula 1

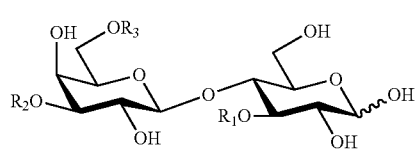

1 wherein $R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, provided that at least one galactosyl residue of a N-acetyl-lactosaminyl or a lacto-N-biosyl group is not substituted,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, provided that at least one galactosyl residue of a N-acetyl-lactosaminyl or a lacto-N-biosyl group is not substituted.

Preferably, compounds of formula 1 are of formulae 1a or 1b

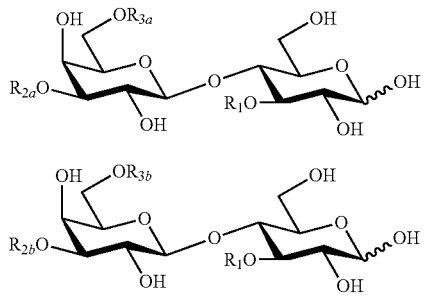

wherein R₁ is as defined above,

R$_{2a}$ is an N-acetyl-lactosaminyl group optionally substituted with another N-acetyl-lactosaminyl group; any N-acetyl-lactosaminyl group can be substituted with one or more sialyl and/or fucosyl residue, but preferably void of a sialyl and/or fucosyl residue, R$_{3a}$ is H or an N-acetyl-lactosaminyl group that can be substituted with a lacto-N-biosyl group if R$_{2a}$ is unsubstituted N-acetyl-lactosaminyl group; any N-acetyl-lactosaminyl and lacto-N-biosyl group can be substituted with one or more sialyl and/or fucosyl residue, but preferably void of a sialyl and/or fucosyl residue, R$_{2b}$ is a lacto-N-biosyl group optionally substituted with sialyl and/or fucosyl residue, but preferably void of a sialyl and/or fucosyl residue, and R$_{3b}$ an N-acetyl-lactosaminyl group optionally substituted with one N-acetyl-lactosaminyl group, or with two N-acetyl-lactosaminyl groups or with one N-acetyl-lactosaminyl group and one lacto-N-biosyl group; any N-acetyl-lactosaminyl and lacto-N-biosyl group can be substituted with one or more sialyl and/or fucosyl residue, but preferably void of a sialyl and/or fucosyl residue.

More preferably, compounds of formulae 1a and 1b have one or more of the following linkages and modifications:

to the N-acetyl-lactosaminyl group of R$_{2a}$, if substituted, another N-acetyl-lactosaminyl group is attached by a 1-3 interglycosidic linkage, the lacto-N-biosyl group, if present in R$_{3a}$, is attached to the N-acetyl-lactosaminyl group by a 1-3 interglycosidic linkage, to the N-acetyl-lactosaminyl group of R$_{3b}$, if substituted, another N-acetyl-lactosaminyl group is attached by a 1-3 interglycosidic linkage, two N-acetyl-lactosaminyl groups are attached by a 1-3 and a 1-6 interglycosidic linkage, and a lacto-N-biosyl group is attached by a 1-3 interglycosidic linkage and a N-acetyl-lactosaminyl group is attached by a 1-6 interglycosidic linkage.

Even more preferably, the carbohydrate acceptor used in the third aspect of the invention is selected from the group consisting of lactose, lacto-N-neotetraose (LNnT), Galβ1-4GlcNAcβ1-3Galβ1-4[Fucα1-3]Glc, lacto-N-hexaose (LNH, Galβ1-3GlcNAcβ1-3[Galβ1-4GlcNAcβ1-6]Galβ1-4Glc), lacto-N-neohexaose (LNnH, Galβ1-4GlcNAcβ1-3[Galβ1-4GlcNAcβ1-6]Galβ1-4Glc), Fucα1-2Galβ1-3GlcNAcβ1-3(Galβ1-4GlcNAcβ1-6)Galβ1-4Glc, Galβ1-3[Fucα1-4]GlcNAcβ1-3[Galβ1-4GlcNAcβ1-6]Galβ1-4Glc, Galβ1-4[Fucα1-3]GlcNAcβ1-6[Galβ1-4GlcNAcβ1-3] Galβ1-4Glc, Fucα1-2Galβ1-3[Fucα1-4]GlcNAcβ1-3 (Galβ1-4GlcNAcβ1-6)Galβ1-4Glc, Fucα1-2Galβ1-4 [Fucα1-3]GlcNAcβ1-6(Galβ1-4GlcNAcβ1-3)Galβ1-4Glc, NeuAcα2-3Galβ1-3GlcNAcβ1-3[Galβ1-4GlcNAcβ1-6] Galβ1-4Glc, sialyl-LNnH I (SLNnH-I, Galβ1-4GlcNAcβ1-3[NeuAcα2-6Galβ1-4GlcNAcβ1-6]Galβ1-4Glc), sialyl-LNnH II (SLNnH-II, Galβ1-4GlcNAcβ1-6[NeuAcα2-6Galβ1-4GlcNAcβ1-3]Galβ1-4Glc), NeuAcα2-3Galβ1-3 [Fucα1-4]GlcNAcβ1-3(Galβ1-4GlcNAcβ1-6)Galβ1-4Glc, NeuAcα2-6Galβ1-4[Fucα1-3]GlcNAcβ1-3(Galβ1-4GlcNAcβ1-6)Galβ1-4Glc, Galβ1-4[Fucα1-3]GlcNAcβ1-3 (NeuAcα2-6Galβ1-4GlcNAcβ1-6)Galβ1-4Glc, and disialyl-LNH II (DSLNH-II, Galβ1-4GlcNAcβ1-6[NeuAcα2-3Galβ1-3[NeuAcα2-6]GlcNAcβ1-3]Galβ1-4Glc), advantageously lactose, LNnT, Galβ1-4GlcNAcβ1-3Galβ1-4[Fucα1-3]Glc, LNH and LNnH.

A mutated α2,6-transsialidase of the first aspect of the invention demonstrates a strong α2,6-selectivity and strong regioselectivity when carrying out the method of the third aspect of the invention. No α2,3-sialylated product can be observed. As a result, the product of the reaction is an α2,6-sialyl saccharide or glycoconjugate, preferably an α2,6-sialyl oligosaccharide or a glycoconjugate comprising α2,6-sialyl oligosaccharide fragment, which oligosaccharide preferably comprises 2-10, more preferably 2-6, particularly 2-4 monosaccharide units, and preferably contains a galactose unit, more preferably a terminal galactose unit at the non-reducing end. Preferably, the mutated α2,6-transsialidase of this invention brings the sialyl residue of an appropriate donor to the 6-position of the terminal galactose in the acceptor, more preferably to the 6-position of galactose in lactose, or, if the acceptor is of formula 1 above, specifically to the 6-position of the terminal unsubstituted galactose in a N-acetyl-lactosaminyl or a lacto-N-biosyl group. Accordingly, a mutated α2,6-transsialidase of this invention is preferably used to synthesize sialylated HMOs in which the sialyl residue is attached to a galactose with α2-6 linkage, preferably the sialylated HMOs listed in Table 2 below (for abbreviations see Urashima et al. *Milk Oligosaccharides*, Nova Science Publishers, N Y, 2011, Table 4 in pp. 14-25).

TABLE 2

| acceptor | product |
| --- | --- |
| lactose | 6'-SL |
| LNnT | LST c |
| Galβ1-4GlcNAcβ1-3Galβ1-4[Fucα1-3]Glc | FLST c |
| LNH | SLNH |
| LNnH | SLNnH-I |
| LNnH | SLNnH-II |
| Fucα1-2Galβ1-3GlcNAcβ1-3(Galβ1-4GlcNAcβ1-6)Galβ1-4Glc | FSLNH |
| Galβ1-3[Fucα1-4]GlcNAcβ1-3[Galβ1-4GlcNAcβ1-6]Galβ1-4Glc | FSLNH-III |
| Galβ1-4[Fucα1-3]GlcNAcβ1-6[Galβ1-4GlcNAcβ1-3]Galβ1-4Glc | FSLNnH-I |

TABLE 2-continued

| acceptor | product |
|---|---|
| fucosylated LNnH | FSLNnH-II |
| Fucα1-2Galβ1-3[Fucα1-4]GlcNAcβ1-3(Galβ1-4GlcNAcβ1-6)Galβ1-4Glc | DFSLNH-I |
| Fucα1-2Galβ1-4[Fucα1-3]GlcNAcβ1-6(Galβ1-4GlcNAcβ1-3)Galβ1-4Glc | DFSLNnH |
| NeuAcα2-3Galβ1-3GlcNAcβ1-3[Galβ1-4GlcNAcβ1-6]Galβ1-4Glc | DSLNH-I |
| SLNnH-I | DSLNnH |
| SLNnH-II | DSLNnH |
| NeuAcα2-3Galβ1-3[Fucα1-4]GlcNAcβ1-3(Galβ1-4GlcNAcβ1-6)Galβ1-4Glc | FDSLNH-III |
| NeuAcα2-6Galβ1-4[Fucα1-3]GlcNAcβ1-3(Galβ1-4GlcNAcβ1-6)Galβ1-4Glc | FDSLNnH |
| Galβ1-4[Fucα1-3]GlcNAcβ1-3(NeuAcα2-6Galβ1-4GlcNAcβ1-6)Galβ1-4Glc | FDSLNnH |
| DSLNH-II | TSLNH |

The sialyl donor used in the third aspect of the invention can be any sialyl compound from which the mutated α2,6-transsialidase of this invention is able to transfer the sialyl residue to a carbohydrate acceptor as described above. Accordingly, in a transsialidase reaction, the sialyl donor can be an α2-6 sialyl saccharide, preferably of 3 or 4 monosaccharide units including the sialyl residue, more preferably 6'-SL, or a compound of formula 2

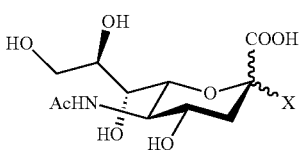

2 wherein X is selected from the group consisting of azide, fluoro, optionally substituted phenoxy, optionally substituted pyridinyloxy, group A, group B, group C and group D

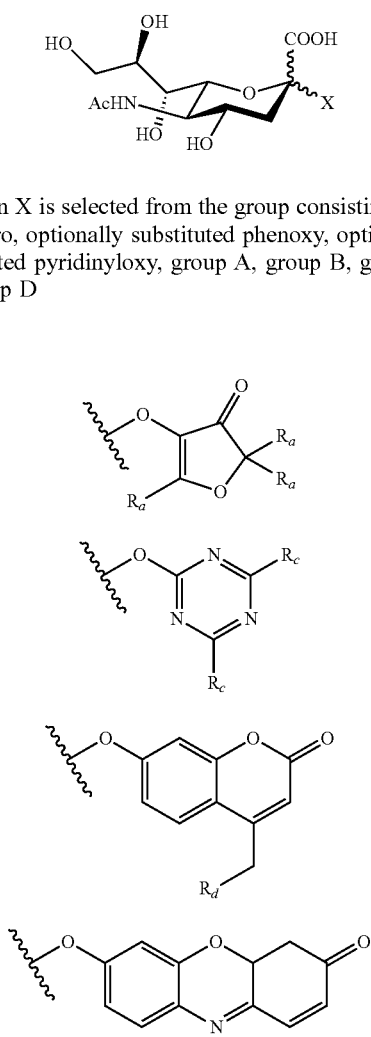

wherein $R_a$ is independently H or alkyl, or two vicinal $R_a$ groups represent a $=C(R_b)_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino, preferably X in formula 2 is selected from the group consisting of phenoxy, p-nitrophenoxy, 2,4-dinitrophenoxy, 2-chloro-4-nitrophenoxy, 4,6-dimethoxy-1,3,5-triazin-2-yloxy, 4,6-diethoxy-1,3,5-triazin-2-yloxy, 2-ethyl-5-methyl-3-oxo-(2H)-furan-4-yloxy, 5-ethyl-2-methyl-3-oxo-(2H)-furan-4-yloxy and 2,5-dimethyl-3-oxo-(2H)-furan-4-yloxy-group. Advantageously, the sialyl donor is 6'-SL. Alternatively, natural sialoglycoconjugates like fetuin, casein glycomacropeptide (cGMP) or polysialic acid, are also suitable sialic acid donors in transsialidase reactions. In sialyl transferase reactions, the sialyl donor is a nucleotide derivative of sialic acid, preferably CMP-sialic acid.

According to a fourth aspect of the invention, the use of a mutated α2,6-transsialidase of the first aspect of the invention is provided for synthesizing a sialylated carbohydrate, preferably an α2-6-sialyl mono- or oligosaccharide, more preferably a sialylated HMO having an α2-6-sialyl residue, even more preferably those in which the sialyl residue is attached to a Gal moiety, further even more preferably those in which the sialyl residue is attached to a terminal Gal moiety, especially sialylated HMOs listed in the Table 2 above, particularly 6'-SL, LST c, FLST c, SLNH, SLNnH-I, SLNnH-II or DSLNnH.

EXAMPLES

In the examples below mutants of *P. leiognathi* JT-SHIZ-119 sialyl transferase truncated by its signal peptide (Δ2-15) were tested, the position(s) of mutation is/are according to SEQ ID No. 1.

Example 1—Single Point Mutants

The determination of activity was performed in potassium phosphate buffer (100 mM, pH=6.0) at 30° C. in 100-200 μl scale using 50 mM of LNnT and 50 mM of 6'-SL with 1/10 volumes of crude enzyme extract. Samples (20 μl) were taken at time points given below. Reactions were stopped by adding 20 μl of a mixture acetonitrile-ammonium formate (10 mM, pH=4.0) 4:1. Subsequently 160 μl of distilled water were added, samples were mixed again, centrifuged and analysed with HPLC (5 μl injection). A Kinetix 2.6μ HILIC 100 A-column (150×4.6 mm) was used at 40° C. column oven temperature with a flow-rate of 2.5 ml/min using 81% of acetonitrile and 19% of ammonium-formate buffer (10 mM, pH=4.0) as mobile phase. Eluted substrates and products were detected at 200 nm.

For all calculations the peak areas of LNnT and the individual sialylated products (compounds A, B and C, see Scheme 1) were normalized according to their respective numbers of N-acetyl residues as follows:
normalized peak area of LNnT=peak area of LNnT
normalized peak area of compound A=½·peak area of compound A
normalized peak area of compound B=½·peak area of compound B
normalized peak area of compound C=⅓·peak area of compound C Selectivity is indicated by calculation of product percentage of compounds A, B and C and calculated as $$\text{product [\%]} = 100 \cdot \frac{\text{product [normalized peak area]}}{\Sigma \text{ products [normalized peak area]} + LNnT\text{[normalized peak area]}}.$$

The concentrations of individual products [mM] were calculated as (assuming that the sum of concentration of LNnT and of all products is 50 mM):

$$\text{product [mM]} = 50 \cdot \frac{\text{product [normalized peak area]}}{\Sigma \text{ products [normalized peak area]} + LNnT\text{[normalized peak area]}}.$$

The total conversion of LNnT to products was calculated as:

$$\text{conversion [\%]} = \frac{100}{50} \cdot \Sigma \text{ products [mM]}.$$

The table below shows the percentages of products generated by wild type enzyme and given mutants after 24 hours. Conversions were 46-67%.

| mutant | compound A (%) | compound B (%) | compound C (%) |
|---|---|---|---|
| wild type | 26 | 23 | 10 |
| A186L | 34 | 17 | 9 |
| A186C | 45 | 8 | 3 |
| A186Y | 42 | 8 | 4 |
| A218F | 44 | 8 | 2 |
| A218I | 43 | 8 | 4 |
| A218V | 42 | 8 | 3 |
| A218Y | 43 | 8 | 3 |
| E180D | 35 | 13 | 7 |
| G156C | 33 | 10 | 4 |
| G156S | 36 | 11 | 7 |
| G156Y | 33 | 16 | 8 |
| G349C | 35 | 11 | 4 |
| G349S | 37 | 12 | 6 |
| G350C | 40 | 13 | 5 |
| G350F | 38 | 14 | 6 |
| G350S | 36 | 13 | 7 |
| G350Y | 32 | 15 | 7 |
| K235C | 37 | 10 | 6 |
| K235H | 33 | 14 | 8 |
| K235R | 38 | 11 | 5 |
| K235V | 37 | 10 | 5 |
| L315C | 36 | 12 | 7 |
| N222C | 38 | 12 | 4 |
| N222D | 37 | 12 | 5 |
| N222F | 35 | 11 | 6 |
| N222R | 36 | 10 | 5 |
| P438H | 33 | 10 | 5 |
| Q161F | 35 | 10 | 5 |
| Q161G | 37 | 12 | 6 |
| R261D | 40 | 11 | 5 |
| R261F | 44 | 8 | 4 |
| R261H | 37 | 10 | 6 |
| R261V | 34 | 17 | 9 |
| T342C | 38 | 6 | 3 |
| Y356F | 37 | 14 | 6 |
| Y356V | 33 | 9 | 5 |
| V242H | 36 | 13 | 7 |

All mutants produced reduced amount of by-products (compounds B and C).

Example 2—Multipoint Mutants

The determination of activity was performed as described in Example 1, and samples were typically taken after 1, 2, 4 and 24 hours. Selectivity is demonstrated by product purity of compound A $$\left(\text{calculated as } 100 \cdot \frac{\text{compound } A \text{ [mM]}}{\text{compound } A \text{ [mM]} + \text{compound } B \text{ [mM]} + \text{compound } C \text{ [mM]}}\right)$$

in function of conversion in the table below.

| mutant | conversion (%) | purity (≥%) | mutant | conversion (%) | purity (≥%) |
|---|---|---|---|---|---|
| wild type | 22 | 92 | G156S-A218Y-N222S-G349C | 20 | 99 |
|  | 36 | 91 |  | 33 | 97 |
|  | 41 | 89 |  | 44 | 96 |
|  | 51 | 77 |  | 54 | 95 |
| A218Y-N222D-G349C | 26 | 96 | G156Y-N222D-G349C | 26 | 96 |
|  | 35 | 97 |  | 31 | 96 |
|  | 45 | 97 |  | 36 | 96 |
| G156Y-A218I-N222D-G349C | 20 | 95 | G156S-A218Y-N222S-G349C | 20 | 94 |
|  | 29 | 95 |  | 39 | 96 |
|  | 48 | 95 |  | 53 | 92 |
| G156S-A218I-N222D-G349S | 22 | 97 | A218Y-N222R-G349S | 20 | 100 |
|  | 33 | 97 |  | 34 | 100 |
|  | 41 | 97 |  | 47 | 99 |
|  | 47 | 96 |  | 54 | 97 |

| mutant | conversion (%) | purity (≥%) | mutant | conversion (%) | purity (≥%) |
|---|---|---|---|---|---|
| A218Y-N222R-G349S-S412P | 20 | 100 | A218Y-N222R-G349S-S412P-D451K | 16 | 100 |
| | 31 | 100 | | 24 | 100 |
| | 48 | 99 | | 47 | 99 |
| | 50 | 95 | | 49 | 97 |

Example 3—Thermostability Improvement of Multipoint Mutants

Thermostabilization of multipoint mutants was verified by determination of the melting temperature ($T_m$) out of inactivation curves. The melting temperature ($T_m$) is the temperature at which 50% of the initial activity of the enzyme remains after 15 min of incubation at elevated temperatures.

Determination of residual activity was performed as described in Example 1. The concentration of mutants and wild type was therefore normalized to the same level. The melting temperatures of mutants are listed in the table below.

| mutant | $T_m$ (° C.) |
|---|---|
| wild type | 43-44 |
| A218Y-N222R-G349S | 47-48 |
| A218Y-N222R-G349S-D458R | 50-51 |
| A218Y-N222R-G349S-D451M | 51-52 |
| A218Y-N222R-G349S-D451L | 52-53 |
| A218Y-N222R-G349S-D451K | 49-50 |
| A218Y-N222R-G349S-T452V | 51-52 |
| A218Y-N222R-G349S-D458F | 51-52 |
| A218Y-N222R-G349S-S400Y | 50-51 |
| A218Y-N222R-G349S-K353I | 51-52 |
| A218Y-N222R-G349S-S412P | 55-56 |
| A218Y-N222R-G349S-S412P-D451K | 57-58 |

Example 4—Demonstration of the Sialyl Transferase and Transsialidase Activity of a Mutant According to the Invention Mutant A218Y-N222R-G349S-S412P-D451K of *P. leiognathi* JT-SHIZ-119 sialyl transferase truncated by its signal peptide (Δ2-15) (the positions of mutations are according to SEQ ID No. 1) was tested in sialyl transferase and transsialidase reactions.

The determination of activity was performed in sodium phosphate buffer (50 mM, pH=6.0; condition A) or in *E. coli* in-vivo like medium (KCl=125 mM, $K_3PO_4$=25 mM, monosodium glutamate=10 mM, $CaCl_2$=1 µM, $MgSO_4$=5 mM, pH=7.5, see García-Contreras et al. *FEBS Journal* 279, 4145 (2012); condition B) using enzyme extract (0.1 g/l) at 30° C. in 1 ml scale. To test the transsialidase activity, the reaction was run with 10 mM of LNnT and 10 mM of 6'-SL. For the sialyl transferase activity, the reaction was run with 10 mM of LNnT or lactose and 10 mM of CMP-sialic acid. Samples (100 µl) were taken at different time points. Reactions were stopped by heating the samples at 90° C. for 10 min. Samples were then centrifuged and supernatants were diluted prior to HPAEC analysis.

The table shows the product formation (LST-c or 6'-SL, in mM) in function of time.

| | LNnT + 6'-SL → LST-c | | LNnT + CMP-sialic acid → LST-c | | lactose + CMP-sialic acid → 6'-SL | |
|---|---|---|---|---|---|---|
| Time (min) | condition A | condition B | condition A | condition B | condition A | condition B |
| 0 | 0.00 | 0.00 | 0.00 | 0.00 | 0.00 | 0.00 |
| 5 min | 0.43 | 0.09 | 0.06 | 0.10 | 0.05 | 0.06 |
| 15 min | 1.24 | 0.22 | 0.10 | 0.16 | 0.09 | 0.09 |
| 30 min | 2.00 | 0.41 | 0.18 | 0.27 | 0.14 | 0.26 |
| 1 h | 3.50 | 0.72 | 0.32 | 0.42 | 0.24 | 0.29 |
| 2 h | 4.55 | 1.26 | 0.61 | 0.72 | 0.44 | 0.56 |
| 3.5 h | 6.07 | 1.87 | 0.88 | 1.20 | 0.68 | 0.83 |
| 18 h | 6.61 | 4.40 | 3.15 | 3.99 | 2.38 | 3.17 |

The results show that the enzyme retained its sialyl transferase activity in the course of protein engineering.

The invention claimed is:

1. A mutated α2,6-transsialidase that comprises an amino acid sequence with at least 60% identity to SEQ ID No: 1, and further comprises at least one mutation selected from the group consisting of:
- at position 156, an amino acid selected from the group consisting of Ser, Thr, Cys, Tyr, Asn, Gln and Trp;
- at position 161, an amino acid selected from the group consisting of Ala, Val, Ile, Leu, Phe, Tyr, Trp and Gly;
- at position 180, an amino acid selected from the group consisting of Asp, Asn and Gln;
- at position 186, an amino acid selected from the group consisting of Val, Ile, Leu, Met, Phe, Tyr, Trp, Ser, Cys and Thr;
- at position 218, an amino acid selected from the group consisting of Val, Ile, Leu, Met, Phe, Tyr, Trp, Cys, Gly and Thr;
- at position 222, an amino acid selected from the group consisting of Gin, Asp, Glu, Cys, Thr, Phe, Tyr, Trp, Arg, Lys and His;
- at position 235, an amino acid selected from the group consisting of Arg, His, Ser, Cys, Ala, Val, Ile and Leu;
- at position 242, an amino acid selected from the group consisting of Arg, His and Lys;
- at position 261, an amino acid selected from the group consisting of His, Lys, Asp, Glu, Ala, Val, Leu and Phe;

at position 315, an amino acid selected from the group consisting of Ser, Thr and Cys;

at position 342, an amino acid selected from the group consisting of Ser and Cys, preferably Cys;

at position 349, an amino acid selected from the group consisting of Ser, Thr and Cys;

at position 350, an amino acid selected from the group consisting of Ser, Thr, Cys, Tyr, Trp and Phe;

at position 356, an amino acid selected from the group consisting of Ala, Val, Ile, Leu, Phe and Trp; and/or at position 438, an amino acid selected from the group consisting of Arg, His and Lys, wherein said mutated α2,6-transsialidase has transsialidase and/or sialyltransferase activity with increased regioselectivity and/or increased thermostability compared to a parent α2,6-transsialidase without the mutation.

2. The mutated α2,6-transsialidase of claim 1 having an improved regioselectivity in a transsialidation reaction compared to a protein having an amino acid sequence which is identical to SEQ ID No: 1.

3. The mutated α2,6-transsialidase of claim 1, wherein the amino acid sequence with at least 60% identity to of SEQ ID No: 1 is a sialyl transferase from *P. leiognathi* JT-SHIZ-119 or its Δ2-15 truncated variant, a sialyl transferase from *P. leiagnathi* JT-SHIZ-145 or its Δ2-15 truncated variant, or a sialyl transferase from *P. damselae* JT0160 or its Δ2-15 truncated variant.

4. The mutated α2,6-transsialidase of claim 1, wherein the at least one mutation is selected from the group consisting of:

at position 156 Gly is substituted by Ser, Thr, Cys, Tyr, Asn, Gln or Trp;

at position 161 Gln or Pro is substituted by Ala, Val, Ile, Leu, Phe, Trp or Gly;

at position 180 Glu is substituted by Asp, Asn, Gln;

at position 186 Ala or Gly is substituted by Val, Ile, Leu, Met, Phe, Tyr, Trp, Ser, Cys or Thr;

at position 218 Ala or Ser is substituted by Val, Ile, Le et, Phe, Tyr, Trp, Cys, Gly or Thr;

at position 222 Asn or Ser is substituted by Gln, Asp, Glu, Cys, Thr, Phe, Tyr, Trp, Arg, Lys or His;

at position 235 Lys or Thr is substituted by Arg, His, Ser, Cys, Ala, Val, Ile or Leu;

at position 242 Val or Leu is substituted by Arg, His or Lys;

at position 261 Arg or Ile is substituted by His, Lys, Asp, Glu, Ala, Val, Leu or Phe;

at position 315 Leu is substituted by Ser, Thr or Cys;

at position 342 Thr is substituted by Ser or Cys;

at position 349 Gly is substituted by Ser, Thr or Cys at position 350 Gly is substituted by Ser, Thr, Cys, Tyr, Trp or Phe;

at position 356 Tyr is substituted by Ala, Val, Ile, Leu, Phe or Trp; and at position 438 Pro is substituted by Arg, His or Lys.

5. The mutated α2,6-transsialidase of claim 4, wherein the amino acid sequence with at least 60% identity to SEQ No: 1 is a sialyl transferase from *P. leiognathe* JT-SHIZ-119 or its Δ2-15 truncated variant, and the at least one mutation is selected from the group consisting of:

at position 156 Gly is substituted by Ser, Cys or Tyr;

at position 161 Gln is substituted by Phe or Gly;

at position 180 Glu is substituted by Asp, at position 186 Ala is substituted by Tyr, Cys or Leu;

at position 218 Ala is substituted by Ile, Val, Phe or Tyr;

at position 222 Asn is substituted by Cys, Asp, Arg or Phe;

at position 235 Lys is substituted by Arg, His, Cys or Val;

at position 242 Val is substituted by His;

at position 261 Arg is substituted by Asp, Phe, His or Val;

at position 315 Leu is substituted by Cys;

at position 342 Thr is substituted by Cys;

at position 349 Gly is substituted by Ser or Cys;

at position 350 Gly is substituted by Ser, Tyr, Phe or Cys;

at position 356 Tyr is substituted by Val or Phe; and at position 438 Pro is substituted by His.

6. The mutated α2,6-transsialidase of claim 1, wherein the at least one mutation comprises at least two mutations at amino acid positions selected from the group consisting of: 156, 218, 222 and 349.

7. The mutated α2,6-transsialidase of claim 6, wherein the at least two mutations comprises at least three mutations at amino acid positions selected from the group consisting of: 156, 218, 222 and 349.

8. The mutated α2,6-transsialidase of claim 1, wherein the at least one mutation comprises the mutations of A218Y, N222R and G349S.

9. The mutated α2,6-transsialidase of claim 1, further comprising a mutation at amino acid position 353, 400 or 450-458.

10. The mutated α2,6-transsialidase of claim 9, wherein the at least one mutation comprises the mutations of A218Y, N222R and G349S, and the mutation at amino acid position 353, 400 or 450-458 comprises at least one mutation selected from the group consisting of: K353I, S400Y, S412P, D451K, D451L, D451M, T452V, D458R and D458F.

11. The mutated α2,6-transsialidase of claim 10, wherein the mutation at amino acid position 353, 400 or 450-458 comprises mutations of S412P and D451K.

12. The mutated α2,6-transsialidase of claim 1, wherein the mutated α2,6-transsialidase has sialyl transferase activity.

13. A process for making a mutated α2,6-transsialidase of claim 1 comprising the steps of:
  a) providing a DNA sequence encoding the mutated α2,6-transsialidase, then
  b) expressing the mutated α2,6-transsialidase in a host cell transformed with the DNA sequence obtained in step a).

14. A method for synthesizing a sialylated saccharide or glycoconjugate comprising the step of reacting a sialyl donor and a saccharide or glycoconjugate as acceptor in the presence of the α2,6-transsialidase according to claim 1 to transfer the sialyl residue of the sialyl donor to the saccharide or glycoconjugate acceptor.

15. The method of claim 14, wherein the acceptor is an oligosaccharide or a glycoconjugate comprising an oligosaccharide having a galactosyl residue.

16. The method of claim 15, wherein the sialyl residue is transferred by the mutated α2,6-transsialidase to attach it to the 6-position of the galactosyl residue.

17. The method of claim 16 resulting in the formation of a sialylated human milk oligosaccharide having a galactosyl residue to which a sialyl residue is attached with an α2-6 linkage.

18. The method of claim 17, wherein the galactosyl residue in the said human milk oligosaccharide is a part of a N-acetyl-lactosaminyl residue.

19. The method of claims 17, wherein the human milk oligosaccharide is 6'-SL, LST c, FLST c, SLNH, SLNnH-I, SLNnH-II, FSLNH, FSLNH-III, FSLNnH-I, FSLnH-II, DFSLNH-I, DSLNnH, DSLNH-I or DSLNnH.

20. A mutated α2,6-transsialidase that comprises an amino acid sequence with at least 90% identity to SEQ ID NO: 1, and further comprises at least one mutation selected from the group consisting of:
  at position 156, an amino acid selected from the group consisting of Ser, Thr, Cys, Tyr, Asn, Gln and Trp
  at position 161, an amino acid selected from the group consisting of Ala, Val, Ile, Leu, Phe, Tyr, Trp and Gly
  at position 180, an amino acid selected from the group consisting of Asp, Asn and Gln
  at position 186, an amino acid selected from the group consisting of Val, Ile, Leu, Met, Phe, Tyr, Trp, Ser, Cys and Thr
  at position 218, an amino acid selected from the group consisting of Val, Ile, Leu, Met, Phe, Tyr, Trp, Cys, Gly and Thr
  at position 222, an amino acid selected from the group consisting of Gln, Asp, Glu, Cys, Thr, Phe, Tyr, Trp, Arg, Lys and His
  at position 235, an amino acid selected from the group consisting of Arg, His, Ser, Cys, Ala, Val, Ile and Leu
  at position 242, an amino acid selected from the group consisting of Arg, His and Lys
  at position 261, an amino acid selected from the group consisting of His, Lys, Asp, Glu, Ala, Val, Leu and Phe
  at position 315, an amino acid selected from the group consisting of Ser, Thr and Cys
  at position 342, an amino acid selected from the group consisting of Ser and Cys
  at position 349, an amino acid selected from the group consisting of Ser, Thr and Cys
  at position 350, an amino acid selected from the group consisting of Ser, Thr, Cys, Tyr, Trp and Phe
  at position 356, an amino acid selected from the group consisting of Ala, Val, Ile, Leu, Phe and Trp; and/or
  at position 438, an amino acid selected from the group consisting of Arg, His and Lys.

* * * * *

SEQUENCE LISTING

<160> NUMBER OF SEQ ID NOS: 3

<210> SEQ ID NO 1
<211> LENGTH: 497
<212> TYPE: PRT
<213> ORGANISM: Photobacterium leiognathi JT-SHIZ-119

<400> SEQUENCE: 1

```
Met Cys Asn Asp Asn Gln Asn Thr Val Asp Val Val Ser Thr Val
1               5                   10                  15

Asn Asp Asn Val Ile Glu Asn Asn Thr Tyr Gln Val Lys Pro Ile Asp
            20                  25                  30

Thr Pro Thr Thr Phe Asp Ser Tyr Ser Trp Ile Gln Thr Cys Gly Thr
        35                  40                  45

Pro Ile Leu Lys Asp Asp Glu Lys Tyr Ser Leu Ser Phe Asp Phe Val
    50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
                85                  90                  95

Ala Pro Thr Leu Glu Val Tyr Val Asp His Ala Ser Leu Pro Ser Leu
            100                 105                 110

Gln Gln Leu Met Lys Ile Ile Gln Gln Lys Asn Glu Tyr Ser Gln Asn
            115                 120                 125

Glu Arg Phe Ile Ser Trp Gly Arg Ile Gly Leu Thr Glu Asp Asn Ala
            130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                165                 170                 175

Leu Asn Leu Glu Leu Asn Thr Asn Thr Ala His Ser Phe Pro Asn Leu
            180                 185                 190

Ala Pro Ile Leu Arg Ile Ser Ser Lys Ser Asn Ile Leu Ile Ser
            195                 200                 205

Asn Ile Asn Leu Tyr Asp Asp Gly Ser Ala Glu Tyr Val Asn Leu Tyr
            210                 215                 220

Asn Trp Lys Asp Thr Glu Asp Lys Ser Val Lys Leu Ser Asp Ser Phe
225                 230                 235                 240

Leu Val Leu Lys Asp Tyr Phe Asn Gly Ile Ser Ser Glu Lys Pro Ser
                245                 250                 255

Gly Ile Tyr Gly Arg Tyr Asn Trp His Gln Leu Tyr Asn Thr Ser Tyr
            260                 265                 270

Tyr Phe Leu Arg Lys Asp Tyr Leu Thr Val Glu Pro Gln Leu His Asp
            275                 280                 285

Leu Arg Glu Tyr Leu Gly Gly Ser Leu Lys Gln Met Ser Trp Asp Gly
            290                 295                 300

Phe Ser Gln Leu Ser Lys Gly Asp Lys Glu Leu Phe Leu Asn Ile Val
305                 310                 315                 320

Gly Phe Asp Gln Glu Lys Leu Gln Gln Glu Tyr Gln Gln Ser Glu Leu
                325                 330                 335

Pro Asn Phe Val Phe Thr Gly Thr Thr Thr Trp Ala Gly Gly Glu Thr
            340                 345                 350

Lys Glu Tyr Tyr Ala Gln Gln Val Asn Val Asn Asn Ala Ile
            355                 360                 365

Asn Glu Thr Ser Pro Tyr Tyr Leu Gly Arg Glu His Asp Leu Phe Phe
    370                 375                 380

Lys Gly His Pro Arg Gly Gly Ile Ile Asn Asp Ile Ile Leu Gly Ser
385                 390                 395                 400

Phe Asn Asn Met Ile Asp Ile Pro Ala Lys Val Ser Phe Glu Val Leu
                405                 410                 415

Met Met Thr Gly Met Leu Pro Asp Thr Val Gly Gly Ile Ala Ser Ser
```

```
              420               425               430
Leu Tyr Phe Ser Ile Pro Ala Glu Lys Val Ser Phe Ile Val Phe Thr
            435               440               445

Ser Ser Asp Thr Ile Thr Asp Arg Glu Asp Ala Leu Lys Ser Pro Leu
450               455               460

Val Gln Val Met Met Thr Leu Gly Ile Val Lys Glu Lys Asp Val Leu
465               470               475               480

Phe Trp Ser Asp Leu Pro Asp Cys Ser Ser Gly Val Cys Ile Ala Gln
                485               490               495

Tyr

<210> SEQ ID NO 2
<211> LENGTH: 483
<212> TYPE: PRT
<213> ORGANISM: Photobacterium leiognathi JT-SHIZ-145

<400> SEQUENCE: 2

Met Cys Asn Asp Asn Gln Asn Thr Val Asp Val Val Ser Thr Val
1               5                   10                  15

Asn Asp Asn Val Ile Glu Asn Thr Tyr Gln Val Lys Pro Ile Asp
                20                  25                  30

Thr Pro Thr Thr Phe Asp Ser Tyr Ser Trp Ile Gln Thr Cys Gly Thr
            35                  40                  45

Pro Ile Leu Lys Asp Asp Glu Lys Tyr Ser Leu Ser Phe Asp Phe Val
        50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
                85                  90                  95

Ala Pro Thr Leu Glu Val Tyr Val Asp His Ala Ser Leu Pro Ser Leu
            100                 105                 110

Gln Gln Leu Met Lys Ile Ile Gln Gln Lys Asn Glu Tyr Ser Gln Asn
        115                 120                 125

Glu Arg Phe Ile Ser Trp Gly Arg Ile Arg Leu Thr Glu Asp Asn Ala
    130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                165                 170                 175

Leu Asn Leu Glu Leu Asn Thr Asn Thr Gly His Ser Phe Arg Asn Ile
            180                 185                 190

Ala Pro Ile Leu Arg Ala Thr Ser Lys Asn Asn Ile Leu Ile Ser
        195                 200                 205

Asn Ile Asn Leu Tyr Asp Asp Gly Ser Ala Glu Tyr Val Ser Leu Tyr
    210                 215                 220

Asn Trp Lys Asp Thr Asp Asn Lys Ser Gln Lys Leu Ser Asp Ser Phe
225                 230                 235                 240

Leu Val Leu Lys Asp Tyr Leu Asn Gly Ile Ser Ser Glu Lys Pro Asn
                245                 250                 255

Gly Ile Tyr Ser Ile Tyr Asn Trp His Gln Leu Tyr His Ser Ser Tyr
            260                 265                 270

Tyr Phe Leu Arg Lys Asp Tyr Leu Thr Val Glu Thr Lys Leu His Asp
        275                 280                 285

Leu Arg Glu Tyr Leu Gly Gly Ser Leu Lys Gln Met Ser Trp Asp Thr
```

```
            290                 295                 300
Phe Ser Gln Leu Ser Lys Gly Asp Lys Glu Leu Phe Leu Asn Ile Val
305                 310                 315                 320

Gly Phe Asp Gln Glu Lys Leu Gln Gln Glu Tyr Gln Gln Ser Glu Leu
                325                 330                 335

Pro Asn Phe Val Phe Thr Gly Thr Thr Thr Trp Ala Gly Gly Glu Thr
            340                 345                 350

Lys Glu Tyr Tyr Ala Gln Gln Val Asn Val Val Asn Asn Ala Ile
                355                 360                 365

Asn Glu Thr Ser Pro Tyr Tyr Leu Gly Arg Glu His Asp Leu Phe Phe
        370                 375                 380

Lys Gly His Pro Arg Gly Gly Ile Ile Asn Asp Ile Ile Leu Gly Ser
385                 390                 395                 400

Phe Asn Asn Met Ile Asp Ile Pro Ala Lys Val Ser Phe Glu Val Leu
                405                 410                 415

Met Met Thr Gly Met Leu Pro Asp Thr Val Gly Gly Ile Ala Ser Ser
                420                 425                 430

Leu Tyr Phe Ser Ile Pro Ala Glu Lys Val Ser Phe Ile Val Phe Thr
        435                 440                 445

Ser Ser Asp Thr Ile Thr Asp Arg Glu Asp Ala Leu Lys Ser Pro Leu
    450                 455                 460

Val Gln Val Met Met Thr Leu Gly Ile Val Lys Glu Lys Asp Val Leu
465                 470                 475                 480

Phe Trp Cys

<210> SEQ ID NO 3
<211> LENGTH: 661
<212> TYPE: PRT
<213> ORGANISM: Photobacterium damselae JT0160

<400> SEQUENCE: 3

Met Cys Asn Ser Asp Asn Thr Ser Leu Lys Glu Thr Val Ser Ser Asn
1               5                  10                  15

Ser Ala Asp Val Val Glu Thr Glu Thr Tyr Gln Leu Thr Pro Ile Asp
                20                  25                  30

Ala Pro Ser Ser Phe Leu Ser His Ser Trp Glu Gln Thr Cys Gly Thr
            35                  40                  45

Pro Ile Leu Asn Glu Ser Asp Lys Gln Ala Ile Ser Phe Asp Phe Val
    50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
    130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
```

-continued

```
            180                 185                 190
Pro Pro Ile Ile Gln Pro Leu Tyr Asn Asn Glu Lys Val Lys Ile Ser
        195                 200                 205
His Ile Ser Leu Tyr Asp Asp Gly Ser Ser Glu Tyr Val Ser Leu Tyr
        210                 215                 220
Gln Trp Lys Asp Thr Pro Asn Lys Ile Glu Thr Leu Glu Gly Glu Val
225                 230                 235                 240
Ser Leu Leu Ala Asn Tyr Leu Ala Gly Thr Ser Pro Asp Ala Pro Lys
                245                 250                 255
Gly Met Gly Asn Arg Tyr Asn Trp His Lys Leu Tyr Asp Thr Asp Tyr
                260                 265                 270
Tyr Phe Leu Arg Glu Asp Tyr Leu Asp Val Glu Ala Asn Leu His Asp
            275                 280                 285
Leu Arg Asp Tyr Leu Gly Ser Ser Ala Lys Gln Met Pro Trp Asp Glu
        290                 295                 300
Phe Ala Lys Leu Ser Asp Ser Gln Gln Thr Leu Phe Leu Asp Ile Val
305                 310                 315                 320
Gly Phe Asp Lys Glu Gln Leu Gln Gln Tyr Ser Gln Ser Pro Leu
                325                 330                 335
Pro Asn Phe Ile Phe Thr Gly Thr Thr Thr Trp Ala Gly Gly Glu Thr
                340                 345                 350
Lys Glu Tyr Tyr Ala Gln Gln Gln Val Asn Val Ile Asn Asn Ala Ile
            355                 360                 365
Asn Glu Thr Ser Pro Tyr Tyr Leu Gly Lys Asp Tyr Asp Leu Phe Phe
        370                 375                 380
Lys Gly His Pro Ala Gly Gly Val Ile Asn Asp Ile Leu Gly Ser
385                 390                 395                 400
Phe Pro Asp Met Ile Asn Ile Pro Ala Lys Ile Ser Phe Glu Val Leu
                405                 410                 415
Met Met Thr Asp Met Leu Pro Asp Thr Val Ala Gly Ile Ala Ser Ser
                420                 425                 430
Leu Tyr Phe Thr Ile Pro Ala Asp Lys Val Asn Phe Ile Val Phe Thr
            435                 440                 445
Ser Ser Asp Thr Ile Thr Asp Arg Glu Glu Ala Leu Lys Ser Pro Leu
        450                 455                 460
Val Gln Val Met Leu Thr Leu Gly Ile Val Lys Glu Lys Asp Val Leu
465                 470                 475                 480
Phe Trp Ala Asp His Lys Val Asn Ser Met Glu Val Ala Ile Asp Glu
                485                 490                 495
Ala Cys Thr Arg Ile Ile Ala Lys Arg Gln Pro Thr Ala Ser Asp Leu
                500                 505                 510
Arg Leu Val Ile Ala Ile Ile Lys Thr Ile Thr Asp Leu Glu Arg Ile
            515                 520                 525
Gly Asp Val Ala Glu Ser Ile Ala Lys Val Ala Leu Glu Ser Phe Ser
        530                 535                 540
Asn Lys Gln Tyr Asn Leu Leu Val Ser Leu Glu Ser Leu Gly Gln His
545                 550                 555                 560
Thr Val Arg Met Leu His Glu Val Leu Asp Ala Phe Ala Arg Met Asp
                565                 570                 575
Val Lys Ala Ala Ile Glu Val Tyr Gln Glu Asp Asp Arg Ile Asp Gln
                580                 585                 590
Glu Tyr Glu Ser Ile Val Arg Gln Leu Met Ala His Met Glu Asp
            595                 600                 605
```

-continued

```
Pro Ser Ser Ile Pro Asn Val Met Lys Val Met Trp Ala Ala Arg Ser
        610             615             620

Ile Glu Arg Val Gly Asp Arg Cys Gln Asn Ile Cys Glu Tyr Ile Ile
625             630             635             640

Tyr Phe Val Lys Gly Lys Asp Val Arg His Thr Lys Pro Asp Asp Phe
            645             650             655

Gly Thr Met Leu Asp
            660
```